Figure 1A:
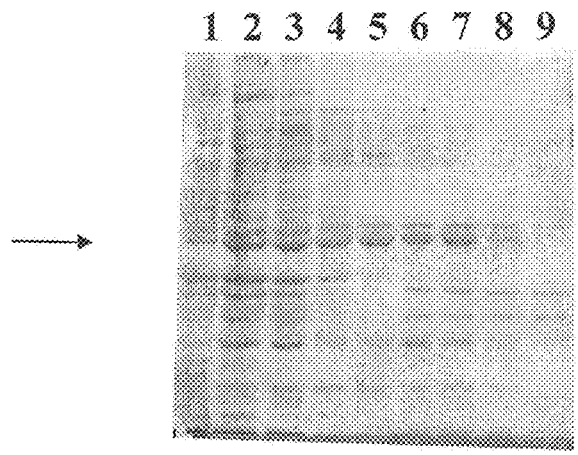

US009862933B2

(12) United States Patent
Ge et al.

(10) Patent No.: US 9,862,933 B2
(45) Date of Patent: Jan. 9, 2018

(54) METHOD FOR IN-VITRO PREPARATION OF DOUBLE-LAYERED VIRUS-LIKE PARTICLES OF ROTAVIRUS

(71) Applicants: Xiamen University, Xiamen (CN); Xiamen Innovax Biotech Co., Ltd., Xiamen (CN)

(72) Inventors: Shengxiang Ge, Xiamen (CN); Tingdong Li, Xiamen (CN); Qingshun Guo, Xiamen (CN); Feihai Xu, Xiamen (CN); Jun Zhang, Xiamen (CN); Ningshao Xia, Xiamen (CN)

(73) Assignees: Xiamen University, Xiamen, Fujian (CN); Xiamen Innovax Biotech Co., Ltd., Xiamen, Fujian (CN)

( * ) Notice: Subject to any disclaimer, the term of this patent is extended or adjusted under 35 U.S.C. 154(b) by 16 days.

(21) Appl. No.: 14/429,586

(22) PCT Filed: Jun. 24, 2013

(86) PCT No.: PCT/CN2013/077736
§ 371 (c)(1),
(2) Date: Mar. 19, 2015

(87) PCT Pub. No.: WO2014/044067
PCT Pub. Date: Mar. 27, 2014

(65) Prior Publication Data

US 2015/0252334 A1 Sep. 10, 2015

(30) Foreign Application Priority Data

Sep. 20, 2012 (CN) .......................... 2012 1 0350365

(51) Int. Cl.
*C12N 7/04* (2006.01)
*C12N 7/00* (2006.01)
(Continued)

(52) U.S. Cl.
CPC .............. *C12N 7/00* (2013.01); *A61K 38/162* (2013.01); *A61K 39/00* (2013.01); *C12N 7/04* (2013.01);
(Continued)

(58) Field of Classification Search
None
See application file for complete search history.

(56) References Cited

FOREIGN PATENT DOCUMENTS

| | | |
|---|---|---|
| EP | 1576877 | 9/2005 |
| FR | 2 806 087 | 9/2001 |
| WO | 2012049366 | 4/2012 |

OTHER PUBLICATIONS

Crawford et al. Characterization of Virus-Like Particles Produced by the Expression of Rotavirus Capsid Proteins in Insect Cells. J. Virol. 1994; 68(9): 5945-5952.*

(Continued)

*Primary Examiner* — Janet L Andres
*Assistant Examiner* — Stuart W Snyder
(74) *Attorney, Agent, or Firm* — Honigman Miller Schwartz and Cohn LLP; Thomas A. Wootton, Esq.; Jonathan P. O'Obrien

(57) ABSTRACT

The invention relates to a method for preparing double-layered virus-like particles of rotavirus in vitro. The method comprises the following steps: purifying rotavirus VP6 proteins from a lysis supernatant, and in vitro assembling double-layered virus-like particles consisting of VP2 proteins and VP6 proteins, wherein the proteins and the virus-like particles can be used for preventing or reducing the clinical symptoms caused by rotavirus infection.

24 Claims, 13 Drawing Sheets

(51) Int. Cl.
 A61K 38/16 (2006.01)
 A61K 39/00 (2006.01)
(52) U.S. Cl.
 CPC .............. C12N 2720/12322 (2013.01); C12N 2720/12323 (2013.01); C12N 2720/12333 (2013.01); C12N 2720/12334 (2013.01); C12N 2720/12352 (2013.01)

(56) References Cited

OTHER PUBLICATIONS

Labbe et al. Expression of Rotavirus VP2 Produces Empty Corelike Particles. J. Virol. 1991; 65(6): 2946-2952.*
T-D Li, Prokaryotic Expression of Rotavirus Structure Protein and In-Vitro Assembly of Virus-like Particles, Chinese Master's Theses Full-text Database Medicine and Health Sciences, Dec. 15, 2009 (Dec. 15, 2009), No. 12, p. E069-19.*
Pennings et al. The Applications of Hydrophobic Interaction Chromatography to the Purification of Plant Proteins. Phytochem. Anal. 1991; 2: 191-198).*
Hanslip et al. Assembly of Human Papillomavirus Type-16 Virus-Like Particles: Multifactorial Study of Assembly and Competing Aggregation. Biotechnol. Prog. 2006, 22, 554-560.*
Andrea Bertolotti-Ciarlet et al., "Immunogenecity and protective efficacy of rotavirus 2/6-virus-like particles produced by a dual baculovirus expression vector and administered intramuscularly, intranasally, or orally to mice", Vaccine 21:3885-3900, 2003.
Tingdong Li, "Prokaryotic Expression of Rotavirus Structure Protein and In-Vitro Assembly of Virus-like Particles", Chinese Master's Thesis Full-text database Medicine and Health Sciences, No. 12, pp. E069-19, 2009.
M. J. Redmond et al., "Assembly of recombinant rotavirus proteins into virus-like particles and assessment of vaccine potential", Vaccine, 11(2):273-281, 1993.
Qinghuan Zhao et al., "Self-Assembled Virus-Like Particles from Rotavirus Structural Protein VP6 for Targeted Drug Delivery", Bioconjugate Chemistry, 22(3):346-352, 2011.

Tingdong Li et al., "Improved characteristics and protective efficacy in an animal model of *E. coli*-derived double-layered rotavirus virus-like particles", Vaccine, 32:1921-1931, 2014 recombinant.
Gonzalez, et al., "Assembly of souble-layered virus-like particles in mammalian cells by coexpression of human rotavirus VP2 and VP6", Journal of General Virology, vol. 76, pp. 2357-2360, Sep. 1995.
International Search Report for PCT/CN2013/077736, dated Sep. 26, 2013.
Li, Tingdong, "Expression of Rotavirus Structure Protein in *Escherichia coli* and Assembly of Virus-like Particles Thereof In Vitro", Chinese Master's Thesis Full-text database Medicine and Health Scinences, No. 12, pp. E069-19, Dec. 15, 2009.
Redmond, et al., "Assembly of recombinant rotavirus proteins into virus-like particles and assessment of vaccine potential", Vaccine, vol. 11, No. 2, pp. 273-281, 1993.
Zhao, et al., "Self-Assembled Virus-Like Particles from Rotavirus Structural Protein VP6 for Targeted Drug Delivery", Biocultural Chemistry, vol. 22, No. 3, pp. 346-352, Feb. 21, 2011.
Bican, Patrick, et al., "Purification and Characterization of Bovine Rotavirus Cores," J of Virology, Sep. 1982, p. 1113-1117.
Charpilienne, Annie et al, "Identification of Rotavirus VP6 Residues Located at the Interface with VP2 that are Essential for Capsid Assembly and Transcriptase Activity," J of Virology, Aug. 2002, p. 7822-7831 (Am Soc for Microbiology).
Crawford, Sue E., et al., Characterization of Virus-Like Particles Produced by the Expression of Rotavirus Capsid Proteins in Insect Cells; J. Virol. 1994; 68(9): 5945-5952.
Hanslip, Simon J., et al., Assembly of Human papillomacirus Type-16 Virus-Like Particles: Multifactorial Study of Assembly and Competing Aggregation; Biotechnol. Prog. 2006. 22, 554-560.
Labbe, Marie, et al., Expression of Rotavirus VP2 Produces Empty Corelike Particles; J. Virol. 1991; 65(6); 2946-2952.
Palomares, Laura A., et al., "Challenges for the Production of Virus-Like Particles in Insect Cells: The Case of Rotavirus-Like Particles," Biochemical Engineering Journal 45 (2009) 158-167.
Pennings, E.J.M., et al., The Applications of Hydrophobic Interaction Chromatography to the Purification of Plant Proteins; Phytochem. Anal. 1991; 2: 191-198.

* cited by examiner

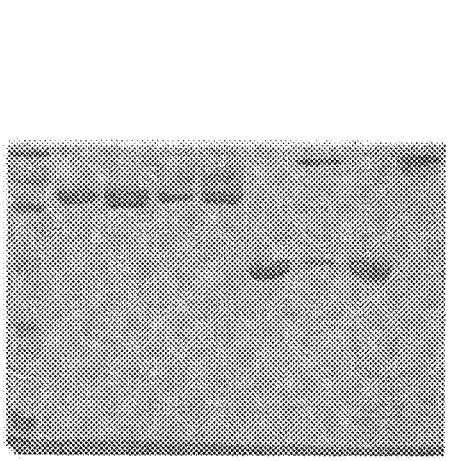
FIG. 3A
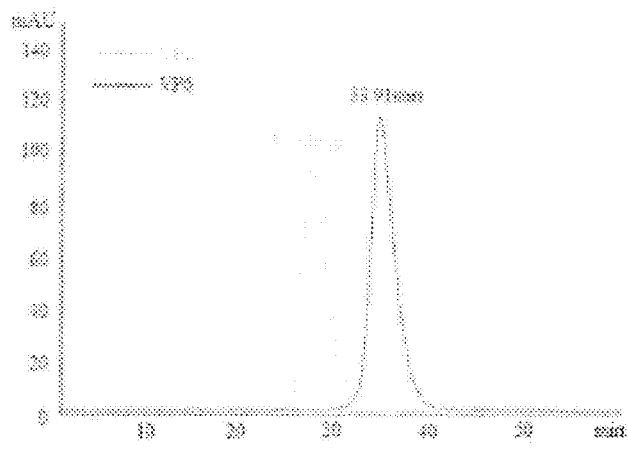
FIG. 3B
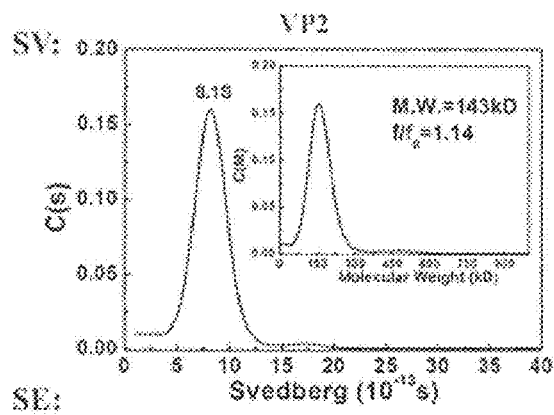
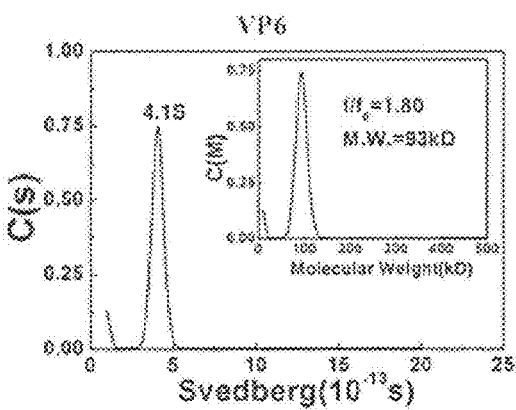
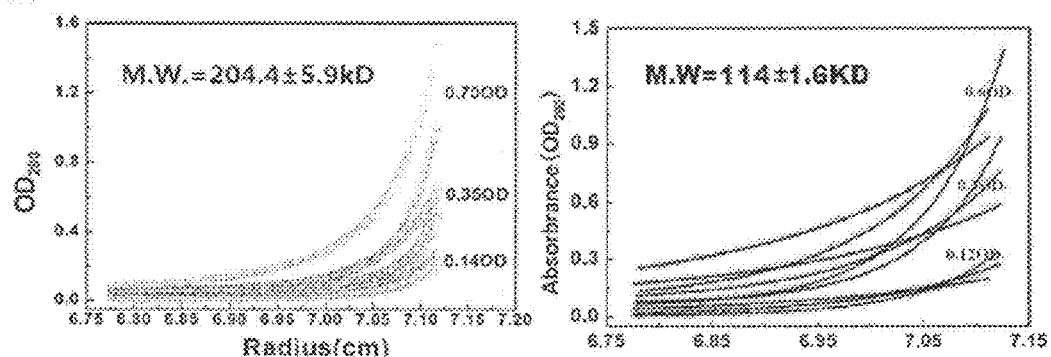
FIG. 3C          FIG. 3D

METHOD FOR IN-VITRO PREPARATION OF DOUBLE-LAYERED VIRUS-LIKE PARTICLES OF ROTAVIRUS

CROSS-REFERENCE

This application claims priority under 35 U.S.C. §371 to Patent Cooperation Treaty application PCT/CN2013/077736, filed Jun. 24, 2013, which claims the benefit of Chinese patent application no. 201210350365.8, filed Sep. 20, 2012, the entire contents of which are incorporated herein by reference.

SEQUENCE LISTING

This application incorporates in its entirety the Sequence Listing entitled "2015-03-18_PCT-CN2013-077736_SeqList_ST25.txt" (1,164 bytes), which was created on Mar. 18, 2015. This sequence listing is filed electronically with the other parts of the application.

FIELD OF THE INVENTION

The invention relates to the fields of biochemistry, molecular biology, and molecular virology; particularly, the invention relates to a structural protein of rotavirus, VP6 protein, a method for preparing the protein, and a method for in vitro assembly of virus-like particles (VLPs) containing the protein, wherein the protein and the VLPs may be useful for preventing or alleviating diarrhea caused by rotavirus infection.

BACKGROUND OF THE INVENTION

Rotavirus (RV) belongs to the rotavirus genus belonging to the Reoviridae family, which is the main pathogen responsible for infant diarrhea and was found in duodenum from patients with gastroenteritis by Bishop in 1973 (Bishop, Davidson et al. 1973). Studies showed that more than 95% of children were infected with rotavirus at least once before 5 years old. According to statistics from WHO, up to 600,000 people died of rotavirus infection annually, cases of diarrhea reached up to 200 million; and in USA only, economic loss caused by rotavirus infection reached up to 100 million dollars annually (Hsu, Staat et al. 2005; Tate, Burton et al. 2011), resulting in serious financial burden and social burden.

Rotavirus is a nonenveloped RNA virus. The genome of rotavirus consists of 11 double-stranded RNA molecules which encode 6 structure proteins (VP1-VP4, VP6 and VP7) and 6 non-structure proteins (NSP1-NSP6) (Estes and Cohen 1989). Rotavirus is icosahedral, and its capsid consists of three concentric layers, i.e. the core layer consisting of VP1, VP2 and VP3, the inner capsid consisting of VP6, and the outer capsid consisting of VP4 and VP7. VP6 is a species-specific antigen, and depending on its antigenicity, rotavirus may be divided into 7 groups, i.e. rotavirus A-G, among which rotavirus A is the main pathogen responsible for diarrhea among infants and young children. The protein has a strong immunogenicity, and although it is not a neutralizing antigen, it can have a good immune protection (Sabara, Frenchick et al. 1994). VP4 and VP7 are the main neutralizing antigens, and, rotavirus A can be divided into serotype P and serotype G depending on the antigenicity of them, and can be divided into different genotypes depending on their genes. G type and P type are independent of each other and are also interacted; the common combinations include G1P[8], G2P[4], G3P[8] and G4P[8]; in recent years, G9P[8] and G9P[6] are more and more popular (Li, Liu et al. 2009).

There are not specific drugs for rotavirus yet, and safe and effective vaccines are the important means for control of rotavirus infection. After years of research undergoing three phases, i.e. monovalent attenuated vaccines, polyvalent gene recombinant vaccines, and genetically engineering vaccines, there are four rotavirus vaccines appeared in the market one by one, including tetravalent human-ape gene recombinant vaccine from Wyeth, monovalent attenuated vaccine from Lanzhou Institute, pentavalent human-bovine gene recombinant vaccine from Merck, and monovalent attenuated vaccine from GSK. However, these vaccines are attenuated live vaccines which have large potential safety hazard, and the vaccines from Wyeth were recalled due to intestinal intussusception half a year after being in the market (Murphy, Gargiullo et al. 2001); although the vaccines from MERCK and GSK were demonstrated to be safe and effective by a large number of clinical tests (Bernstein, Sack et al. 1999; Vesikari, Matson et al. 2006; Linhares, Velazquez et al. 2008; Vesikari, Itzler et al. 2009; Snelling, Andrews et al. 2011), in countries and regions with a high rotavirus mortality such as Asia and Africa, the protection efficiency was much lower than that in developed countries such as Europe and America (Armah, Sow et al. 2010; Zaman, Anh et al. 2010; Madhi, Cunliffe et al. 2011). More and more evidence showed that upon vaccination with these two vaccines, shedding of virus occurred and horizontal transmission of virus might occur (Anderson 2008; Rivera, Pena et al. 2011; Yen, Jakob et al. 2011). It was also shown in some studies that serious gastroenteritis might be developed in children with immunologic deficiency after vaccination with the vaccines (Steele, Cunliffe et al. 2009; Patel, Hertel et al. 2010). The vaccines from Lanzhou Institute have been commercially available for more than 10 years, and no serious problem is found yet; however, they can only prevent serious diarrhea, and cannot prevent rotavirus infection (Fu, Wang et al. 2007). Therefore, although delightful results are obtained in studies on attenuated vaccines for rotavirus, there are also some problems and the safety and effectiveness need to be further improved. It is imperative to develop more safe and effective vaccines. Non-replicating vaccines are the main direction for studies on rotavirus vaccines now, and genetically engineering vaccines attract much attention because of the characteristics such as low cost, safety and effectiveness.

Genetically engineering vaccines mainly refer to antigens of rotavirus expressed by genetically engineering methods, which are used to immunize animal or human so as to achieve immune protection. Such vaccines include nucleic acid vaccines, synthetic peptide vaccines, recombinantly expressed antigen vaccine, and virus-like particles (VLPs) vaccines. The effectiveness and safety of VLPs vaccines now have been sufficiently demonstrated in the case of HBV, HEV and HPV vaccines, and have become a new generation of candidate vaccines with the greatest research value, as well recognized globally. The studies on RV-VLPs vaccines started in 80s of the last century, and a lot of animal experimental results showed that RV-VLP vaccines had good protective effect and could mediate a broad heterogenic protection.

RV-VLP refers to virus-like particle consisting of structure proteins, which is similar to native virus particle in terms of shape and structure and retains the native conformation of virus particle without containing viral nucleic acids. The particles can be divided into two classes; one class is a trilayer particle consisting of VP2, VP4, VP6 and VP7, or a double-layered particle consisting of VP6 & VP4, VP7, both of which can stimulate the generation of neutralizing antibodies in organisms (Crawford, Estes et al. 1999; Jiang, Estes et al. 1999); and the other class is a double-layered particle consisting of VP2 and VP6, and a monolayer particle consisting of VP6, which cannot stimulate the generation of neutralizing antibodies in organisms as they contain no neutralizing antigen, but also have a good protective effect as they can stimulate enhanced cell immunity in organisms (Coste, Sirard et al. 2000; Yuan, Geyer et al. 2000; Nguyen, Iosef et al. 2003); since variation in VP6 is relatively low, the particle can lead to a broad heterogenic protection. Relative to the first class of particles, the second class of particles have the same protective effect, but comprise less components, which greatly reduces processing difficulty and cost and thus are more favored.

The key for VP2/6-VLP vaccine development is to produce homogeneous VLP samples efficiently in a large amount. Insect baculovirus expression systems are commonly used now, and the rotavirus structure proteins VP2 and VP6 co-expressed in the system may self-assemble into VLP (Bertolotti-Ciarlet, Ciarlet et al. 2003). However, eukaryotic expression systems have the shortcomings such as high cost, long period, complex operations, and low expression level, and non-specific proteins and nucleic acids are generally encapsulated during the assembly, and thus it is difficult to achieve high-efficient and controllable assembly (Palomares and Ramirez 2009). Although there are studies on in vitro assembly of rotavirus VLP particles, the further development of RV VLP vaccines are restricted due to low yield.

Prokaryotic expression system has advantages such as low cost and simple operation. However, since prokaryotic expression system lacks specific posttranslational modifications, many proteins form inclusion bodies in prokaryotic expression. In current, there are studies showing that structure proteins of rotavirus were expressed in prokaryotic system, including VP6, VP4 and VP7, which were either expressed in inclusion bodies and unable to be renatured effectively (Zhao, Chen et al. 2011), or expressed in a fusion form (Choi, Basu et al. 2000). Although fusion expression is favorable for the purification of desired proteins, expensive enzymes are generally required for cleavage of fusion proteins. Thus, prokaryotic expression system is not suitable for large-scale production.

Therefore, this field still demands techniques with low cost which can achieve high-efficient and controllable assembly and produce rotavirus structure proteins and virus-like particles at a large scale.

DESCRIPTION OF THE INVENTION

The object of the invention is to provide a novel method for preparing double-layered virus-like particles of rotavirus, wherein the double-layered particles consist of rotavirus VP2 protein and VP6 protein.

The inventors discovered surprisingly after the research that structural protein VP6 of rotavirus may be expressed in E. coli in a soluble form, and the purified VP6 is present in a form of trimer and may be self-assembled into a monolayer virus-like particle 6-VLP or assembled with VP2 in a VLP state or in a non-VLP state to form a double-layered virus-like particle 2/6-VLP; and the VP6 protein and VLPs thereof can be used for preventing or reducing clinical symptoms caused by rotavirus infection.

Therefore, the invention relates to VP6 protein of rotavirus A, which is expressed in E. coli and purified; in vitro assembly of the virus-like particle 2/6-VLP comprising the protein; and use of the VP6 protein and VLPs thereof in the prevention or alleviation of diarrhea caused by rotavirus infection. The invention is described as follows.

1. The invention relates to a method for purifying rotavirus VP6 protein in E. coli, comprising expressing the protein in E. coli expression system and purifying the lysis supernatant containing the protein.

In a preferred embodiment, the method for obtaining VP6 protein comprises:
a) expressing VP6 protein in an E. coli expression system;
b) lysing the E. coli expressing the VP6 protein, and separating the supernatant;
c) to the supernatant obtained in step b), adding 0.05%-0.5% polyethyleneimine (PEI) or analog thereof, or adding 10-80 mM metal ions such as $MnCl_2$, $MgCl_2$, $CaCl_2$, $CuCl_2$ and $AlCl_3$, to precipitate nucleic acids and some undesired proteins, and separating the supernatant;
d) adding ammonia sulfate to the supernatant obtained in step c), and collecting the precipitate after sufficient precipitation;
e) re-dissolving the precipitate obtained in step d) in a high-salt buffer, and separating the solution, wherein the solution contains the VP6 protein with a purity of at least 85%;
f) further purifying the VP6 protein with a purity of at least 85% obtained in step e) by chromatography to get the VP6 protein with a purity of above 98%, wherein the purified VP6 protein is identified to be present in a non-particulate form in the solution.

2. In another aspect, the invention relates to in vitro assembly process of double-layered virus-like particle 2/6-VLP of rotavirus.

In a preferred embodiment, the in vitro assembly process of 2/6-VLP is as follows. The purified VP6 protein is mixed with VP2 protein in a non-particulate form, and the buffer is replaced with an assembly buffer. The process mainly comprises the following aspects:
a) the assembly buffer has a pH of between 3.0 and 7.0, preferably between 4.0 and 6.4, most preferably 6.4;
b) the assembly buffer contains 0-2M salt, preferably NaCl, more preferably 150 mM-1M NaCl, and most preferably 300 mM NaCl;
c) the ratio of VP2 protein and VP6 protein by mass is between 1:1 and 1:10, preferably between 1:2 and 1:3, most preferably 1:2.6.

3. In another aspect, the invention relates to use of VP6, 6-VLP and 2/6-VLP in the prevention or alleviation of diarrhea caused by rotavirus infection. The immunization route includes, but is not limited to subcutaneous immunization and muscular injection, and the adjuvant includes, but is not limited to aluminum adjuvant and Freund's adjuvant.

DEFINITIONS OF TERMS IN THE INVENTION

According to the invention, the term "E. coli expression system" refers to an expression system consisting of E. coli (strains) and vectors, wherein the E. coli (strains) are commercially available, including but not limited to: ER2566, BL21(DE3), TG1, DH5α and JM109.

According to the invention, the term "vectors" refers to a nucleic acid carrier tool which can have a polynucleotide encoding a protein inserted therein and allow for the expression of the protein. The "vector" can have the carried genetic material expressed in a host cell by transformation, transduction, or transfection into the host cell. For example, the "vector" includes plasmids, phages, cosmids and the like.

According to the invention, the term "chromatography" includes, but is not limited to: ion exchange chromatography (e.g. Cation exchange chromatography), hydrophobic interaction chromatography, adsorption chromatography (e.g. hydroxyapatite chromatography), gel filtrate chromatography (gel exclusion chromatography), and affinity chromatography.

According to the invention, in the method for obtaining VP2 and VP6 proteins, the term "buffer" refers to a solution which can maintain pH value stable within a certain range, including but not limited to: Tris-HCl buffers, phosphate buffers, HEPES buffers, and MOPS buffers.

According to the invention, the disrupting of the prokaryotic host cell can be achieved by one or more conventional methods, including but not limited to one or more of disruption by a homogenizer, ultrasonic treatment, grinding, high-pressure homogenization, and lysozyme treatment.

According to the invention, in the method for obtaining VP6 protein, the salts used include, but are not limited to: neutral salts, especially alkali metal salt, ammonium salts, hydrochlorides, sulfates, bicarbonates, phosphate salts or biphosphates, especially one or more of NaCl, KCl, $NH_4Cl$, $(NH4)_2SO_4$. NaCl is preferred.

According to the invention, in the method for obtaining VP6 protein, the polyethyleneimine and analog thereof refer to polymers having positive charges on surface, including, but not limited to linear polyethyleneimine, branched polyethyleneimine and derivatives thereof, with a molecular weight of between 1300 and 750000, preferably polyethyleneimine with a molecular weight of 750000.

According to the invention, in the method for obtaining VP6 protein, the divalent and trivalent metal ions include, but are not limited to $Ca^{2+}$, $Mn^{2+}$, $Mg^{2+}$, $Zn^{2+}$, $Cu^{2+}$, $Al^{3+}$ and the like, preferably $Ca^{2+}$ and $Mn^{2+}$, most preferably $Ca^{2+}$.

According to the invention, in the method for obtaining virus-like particle 2/6-VLP, the buffer refers to a solution that is stable within a weak acidic pH range (pH3.0-7.0), including, but not limited to, phosphate buffer, MES buffer, citrate buffer, and the like.

Beneficial Effect of the Invention

Presently, eukaryotic expression systems are used in the preparation of rotavirus VLPs, and the insect-baculovirus expression system is the most commonly used.

The VP2 and VP6 proteins expressed in eukaryotic expression systems are closer to naturally occurring proteins in terms of conformation, and can self-assemble into VLPs in vivo. However, eukaryotic expression systems have the shortcomings, such as long expression period, complex operation, low expression level, non-specific encapsulation of undesired proteins and nucleic acids in assembly process, especially the formation of different types of virus-like particles during co-expression of several proteins, and difficulty in subsequent purification, and thus can hardly achieve assembly in a high efficient and controllable manner. It is quite difficult to apply a eukaryotic expression system to industrial production in a large scale.

Prokaryotic expression system, especially *E. coli* expression system has advantages such as low cost, short period, and high expression level, and are the most commonly used and well established expression system for recombinant proteins. However, the rotavirus capsid protein expressed in *E. coli* expression system is generally unable to form a correct confirmation and is in a form of inclusion body, while the protein in inclusion body is difficult to be renaturated, and the efficiency is low. Thus, it is difficult to apply a prokaryotic expression system to a large-scale production. Fusion expression can accomplish soluble expression of VP6, but expensive enzymes are generally required for cleavage of a fusion protein generally. Thus, fusion expression cannot be applied to a large-scale production.

In the invention, the capsid protein VP6 of rotavirus A is expressed in the *E. coli* expression system; most of nucleic acids and some undesired proteins can be removed by a pretreatment of PEI or metal ion precipitation, and the VP6 protein is still kept in supernatant in a soluble form. After salting-out and chromatographic purification, VP6 protein with a purity of above 95% can be obtained. After analysis, the protein is present in a form of trimer in the solution, i.e. retains the correct conformation of VP6 protein. The process has the advantages such as simple operation, low cost and high yield, and thus can be applied to industrial production in a large scale. The purified VP6 protein obtained by said steps can be self-assembled into a monolayer particle 6-VLP, and can also be co-assembled with VP2 in a particulate or non-particulate state to form a double-layered particle 2/6-VLP. The process is simple and controllable, and has an assembly efficiency of above 95%, significantly higher than the efficiency of self-assembly of the protein expressed in a eukaryotic cell. As verified experimentally in mice, VP6 protein and its VLPs obtained by prokaryotic expression have high immunogenicity and good protective effect, and are potential as a candidate vaccine for rotavirus.

Therefore, the invention has the following advantages. The preparation method of the invention neither needs high cost and complex process (as eukaryotic expression needs), nor needs expensive enzymes, and are convenient with respect to operation and cheap with respect to cost. Moreover, the preparation method retains the correct conformation of VP6 since the purification process does not undergo drastic denaturation and renaturation. The protein may be self-assembled into 6-VLP or co-assembled with VP2 to form 2/6-VLP, has a good immunogenicity, and exhibits a good immune protection in mouse experiments. The methods of the invention for preparing VP6 protein and virus-like particles (VLPs) thereof may be applied to industrial production in a large scale. The VP6 protein and VLPs thereof of the invention may be used for preventing diarrhea caused by rotavirus infection.

The embodiments of the invention are further described in detail by reference to the drawings and examples. However, a person skilled in the art would understand that the following drawings and examples are intended for illustrating the invention only, rather than defining the scope of the invention. According to the detailed description of the following drawings and preferred embodiments, various purposes and advantages of the invention are apparent for a person skilled in the art.

DESCRIPTION OF THE DRAWINGS

FIG. 1 shows the 10% SDS-PAGE result of VP6 protein in different purification phases of Example 1. FIG. 1A shows the PEI precipitation result, 1: lysis supernatant, 2-9: the results of 40% ammonia sulfate precipitation at different PEI concentrations, 2: 0% PEI, 3: 0.05% PEI; 4: 0.08% PEI; 5: 0.1% PEI; 6: 0.15% PEI; 7: 0.2% PEI, 8: 0.3% PEI; 9: 0.5% PEI. FIG. 1B shows the result of metal ion precipitation+ 40% ammonia sulfate precipitation, 1: 20 mM $MnCl_2$, 2: 10 mM $CaCl_2$, 3: 20 mM $CaCl_2$, 4: 50 mM $CaCl_2$, 5: 100 mM $CaCl_2$; wherein the purity is the highest at 20 mM $CaCl_2$. FIG. 1C shows the result of 20 mM $CaCl_2$ precipitation→25% ammonia sulfate precipitation→Phenyl-HP purification, 1: bacterial lysis supernatant; 2: the supernatant after CaCl$_2$ precipitation; 3: the supernatant obtained after dissolving the precipitate of ammonia sulfate precipitation; 4: the fraction eluted by Phenyl-HP 2M NaCl. The results show that the purity of VP6 is increased from about 10% to about 85% after crude purification by divalent ion precipitation and ammonia sulfate precipitation, and reaches above 98% after further purification through hydrophobic chromatography.

Figure 2:
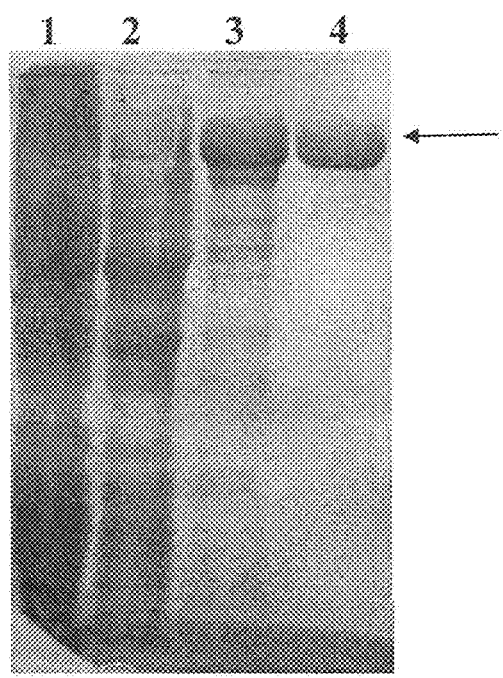

FIG. 2 shows the 10% SDS-PAGE result of VP2 protein in different purification phases of Example 2. 1: bacterial lysis supernatant; 2: the supernatant after PEI precipitation; 3: the supernatant obtained after dissolving the precipitate of ammonia sulfate precipitation; 4: the fraction eluted by SP FF 500 mM NaCl. The results show that the purity of VP2 is increased from about 5% to about 80% after crude purification through PEI precipitation and ammonia sulfate precipitation, and reaches about 95% after further purification through cation exchange chromatography.

FIG. 3 shows results of the SDS-PAGE, size exclusion chromatography and analytical ultracentrifugation identification of the purified VP2 protein and VP6 protein. Figure A shows the results of SDS-PAGE identification, 1: molecular weight Marker; 2-5: purified VP2 protein, 6-9: purified VP6 protein, wherein 2&5 represent the results using a loading buffer containing mercaptoethanol, with a water bath at 100° C. for 10 min; 3&6 represent the results using a loading buffer containing mercaptoethanol, without heating treatment; 4&8 represent the results using a loading buffer containing no mercaptoethanol, with a water bath at 100° C. for 10 min; 5&9 represent the results using a loading buffer containing no mercaptoethanol, without heating treatment. As can be seen, both the VP2 protein and the VP6 protein have a purity of above 95%, wherein the VP2 protein is present in a form of monomers possibly because SDS interrupts the interaction among VP2 monomers; while the VP6 protein is present in a form of polymers. Figure B shows the results of Sepherdex200 size exclusion chromatographic identification of the purified VP2 protein and VP6 protein; the retention time for the VP2 protein and VP6 protein is 27.34 min and 33.91 min, respectively. FIG. 3C shows the result of the analytical ultracentrifugation identification of the VP2 protein, wherein the molecular weight is 204.4±5.6 KDa, which is close to the molecular weight of dimer. FIG. 3D shows the result of the analytical ultracentrifugation identification of the VP6 protein, wherein the molecular weight is 114.9±1.6 KDa, which is close to the molecular weight of trimer.

Figure 4:
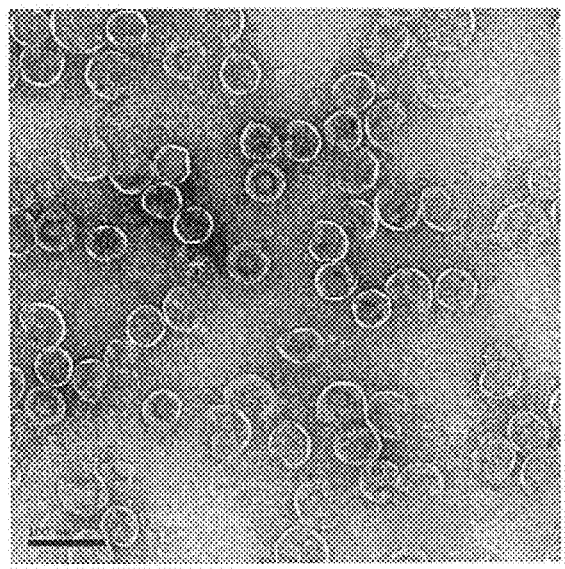

FIG. 4 shows the result of the transmission electron microscopy (TEM) of RV virus-like particle 2-VLP in Example 4, wherein a large number of virus-like particles with a diameter of 50-60 nm can be observed, which is consistent with the theoretical value.

Figures 5A, 5B:
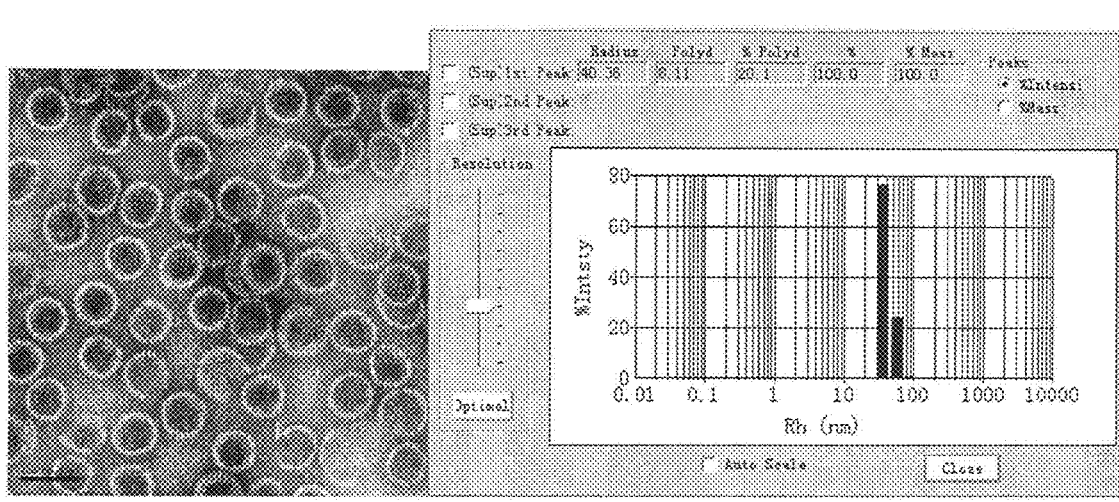
Figure 5C:
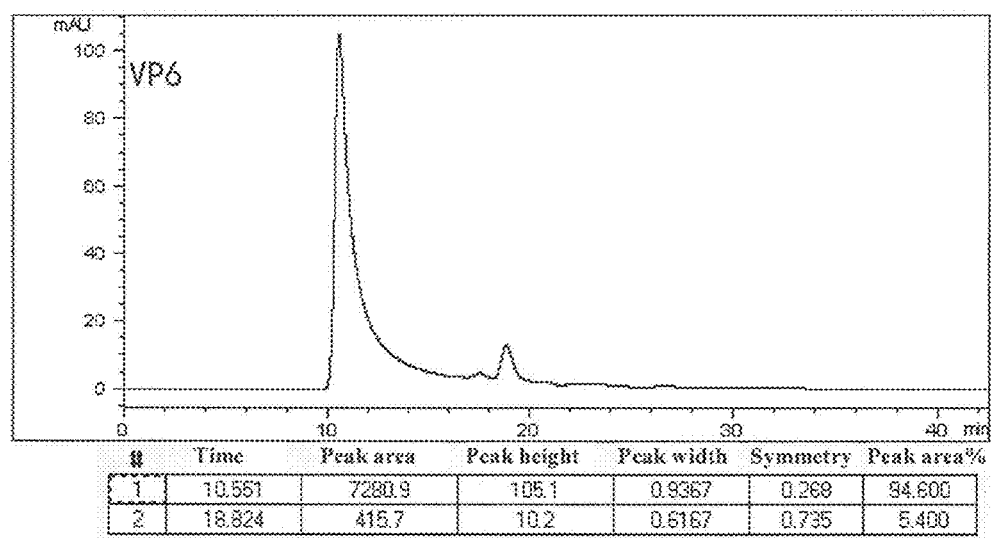

FIG. 5 shows the identification results of the virus-like particle 6-VLP obtained in Example 5. A: the result of the transmission electron microscopy (TEM), wherein a large number of particles with a diameter of about 70 nm are observed, and the structure is relatively loose; B: the result of the dynamic light-scattering measurement, wherein 6-VLP had a hydrodynamic radius of 40.36 nm and a particle assembly rate of 100%; C: the result of the G5000PWXL size exclusion chromatography, wherein 6-VLP has a retention time of 10.551 min and a particle assembly efficiency of higher than 95%.

FIG. 6 shows the identification result of virus-like particle 2/6-VLP assembled by a two-step method in Example 5. A: the result of the analytical ultracentrifugation; B: the TEM result at pH6.0, wherein virus-like particles with a diameter of about 60 nm are observed.

Figure 7:
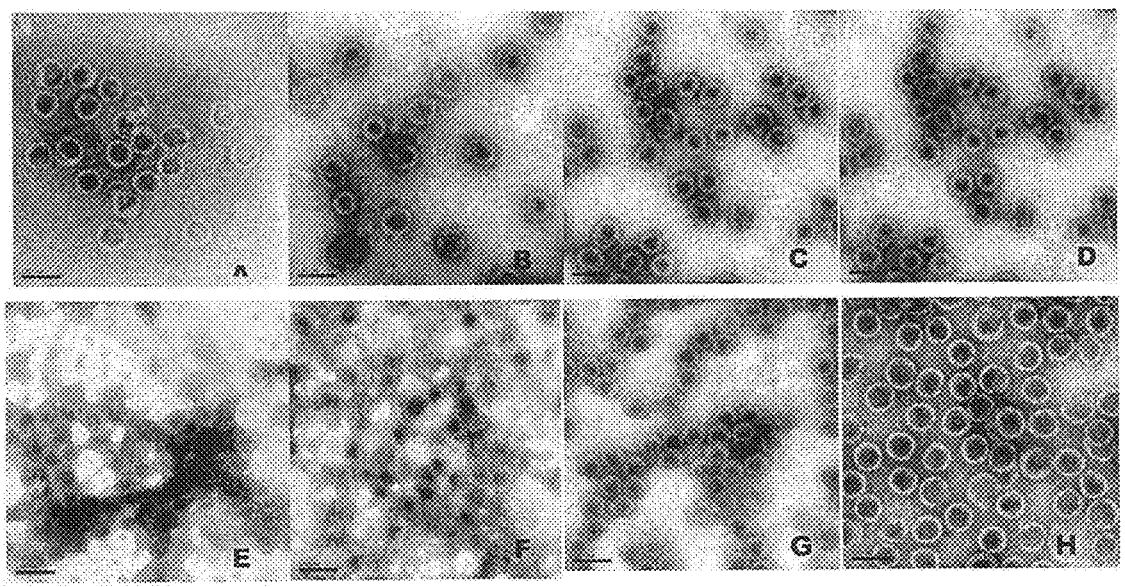

FIG. 7 shows the identification results of 2/6-VLP in different buffer systems in Example 5. A: 50 mM MES6.0, wherein a large number of monolayer particles with a diameter of about 70 nm are observed; B: 50 mM MES6.0+150 mM NaCl, wherein monolayer particles with a diameter of about 70 nm and double-layered particles with a diameter of about 60 nm are observed; C: 50 mM MES6.0+300 mM NaCl, wherein double-layered particles with a diameter of about 60 nm are observed, which are uniform in size; D: 50 mM MES6.0+500 mM NaCl, wherein double-layered particles with a diameter of about 60 nm are observed, which are uniform in size; E: PB5.8+300 mM NaCl, wherein double-layered particles with a diameter of about 60 nm are observed; F: PB6.0+300 mM NaCl, wherein double-layered particles with a diameter of about 60 nm are observed; G: PB6.4+300 mM NaCl, wherein double-layered particles with a diameter of about 60 nm are observed, which are uniform in size; H: 6-VLP control, wherein monolayer particles with a diameter of about 70 nm are observed.

Figure 8A:
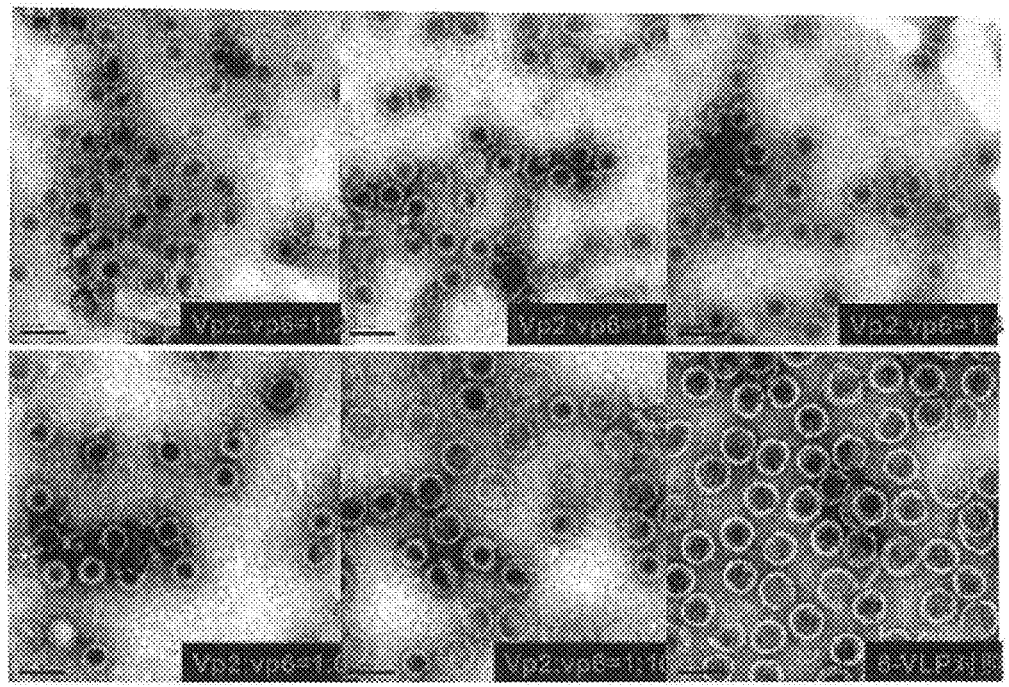
Figure 8B:
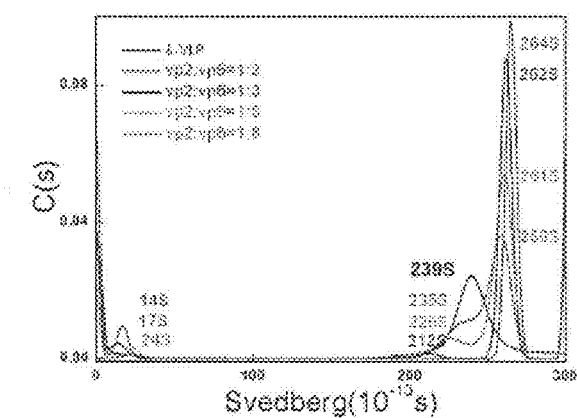
Figure 8C:
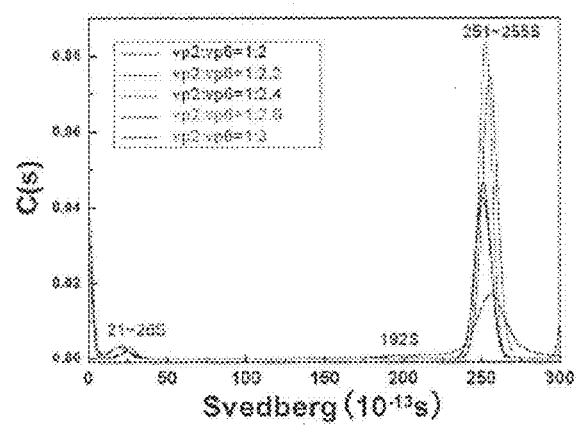

FIG. 8 shows the identification results of 2/6-VLP at different ratios of VP2 and VP6 in Example 5. A: the TEM results: at a ratio of VP2 and VP6 by mass ranging from 1:2 to 1:6, double-layered particles 2/6-VLP with a diameter of about 60 nm are observed; while at a ratio of VP2 and VP6 by mass being 1:10, both 2/6-VLP with a diameter of about 60 nm and 6-VLP with a diameter of about 70 nm are observed; B and C: the results of analytical ultracentrifugation of 2/6-VLP assembled by a two-step method in Example 4, wherein the sedimentation coefficient is within 251-264 S, and the best mass ratio of VP2 and VP6 is 1:2.6.

Figure 9A:
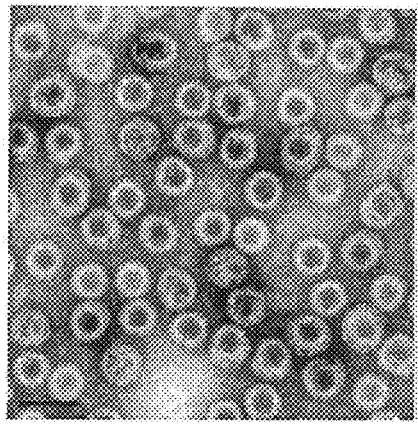
Figure 9B:
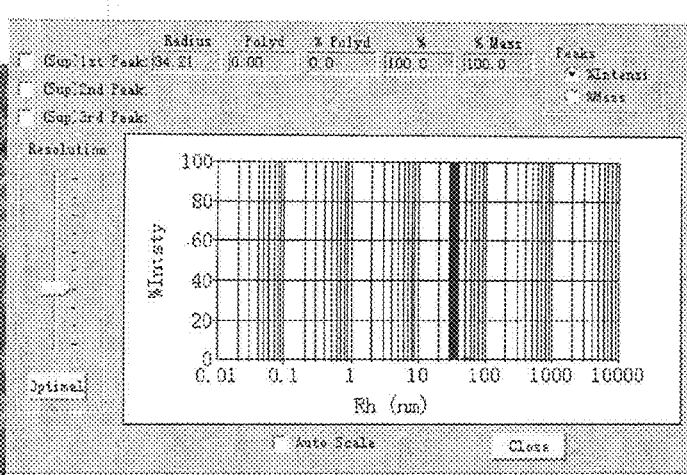

FIG. 9 shows the identification results of 2/6-VLP under the optimal conditions in Example 5. A: the TEM result, wherein a large number of virus-like particles with a diameter of about 60 nm are observed, which are in a double-layered structure and are uniform in size, and the size and shape of which are identical to the theoretic size and shape; B: the results of the dynamic Light-Scattering, wherein the hydrodynamic radius is 34.27 nm, and the particle assembly rate is 100%; C: the results of the G5000PWXL size exclusion chromatography, wherein 2/6-VLP has a retention time of 10.821 min and has an assembly efficiency of above 95%.

Figure 10:
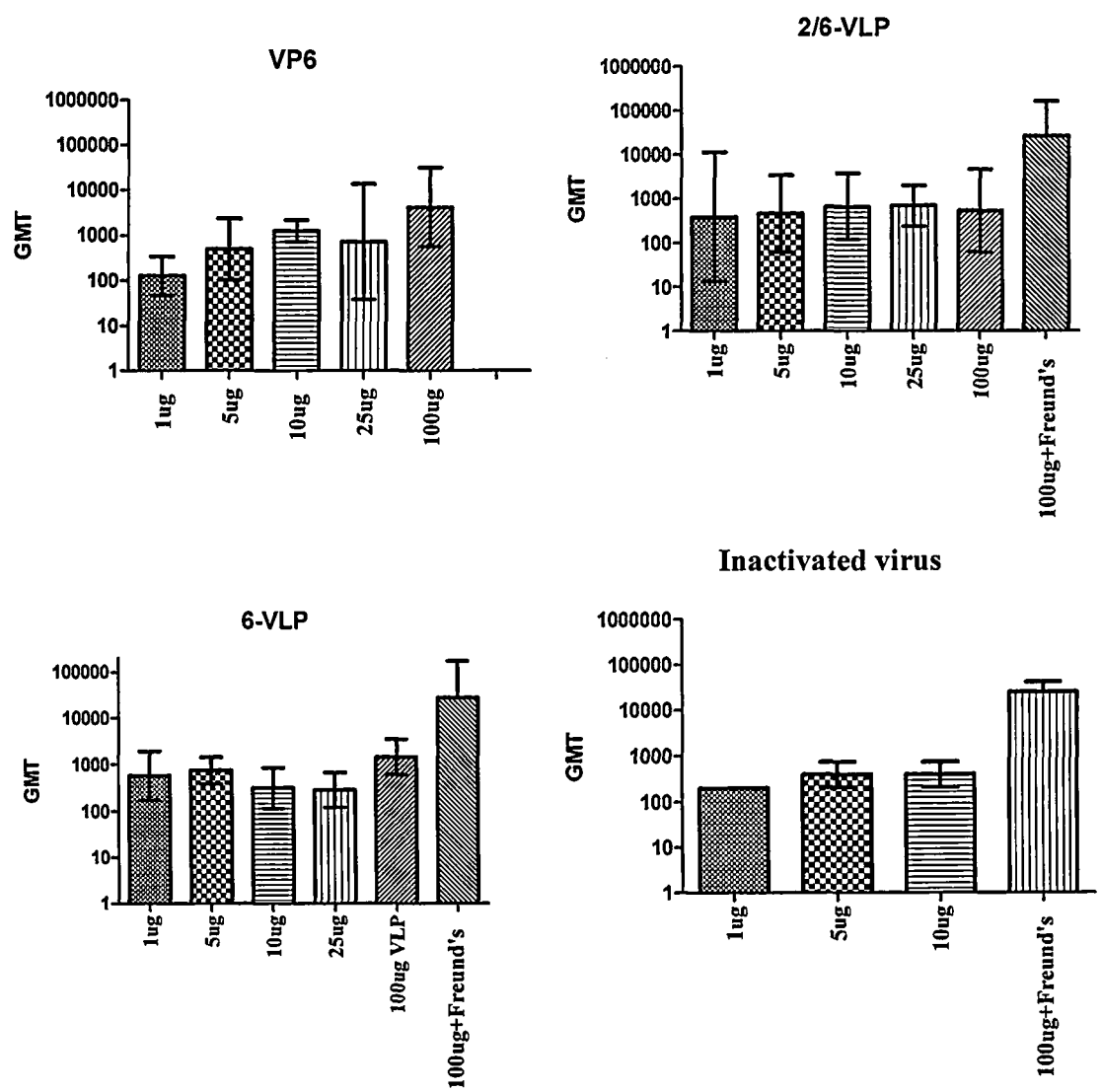

FIG. 10 shows the VP6 antibody titer in sera of mice immunized by VP6 protein of Example 1, 6-VLP and 2/6-VLP of Example 5 and rotavirus A obtained by MA104 cell culture, respectively, wherein as compared with the cultured virus, VP6, 6-VLP and 2/6-VLP have a higher immunogenicity.

FIG. 11 shows the antibody titer against VP6 in sera of mother mice and neonatal mice immunized for three times by muscular injection of VP6 protein of Example 1, 6-VLP and 2/6-VLP of Example 5 and rotavirus A obtained by MA104 cell culture at a dosage of 10 μg, respectively, wherein A shows the antibody titer in sera of mother mice from different immunization groups, and B shows the antibody titer in sera of neonatal mice from different immunization groups.

Figure 12:
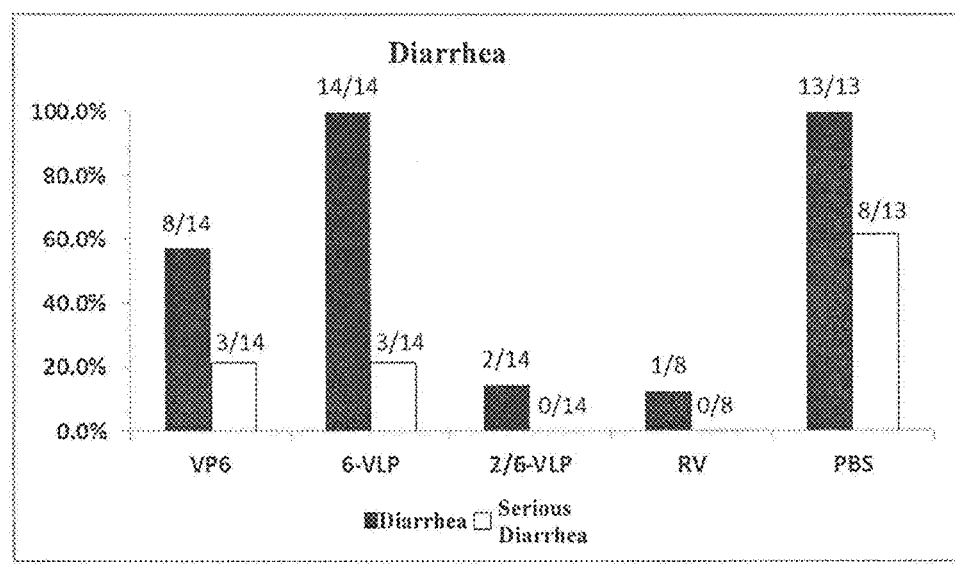

FIG. 12 shows the effect of the antibodies from the mother mice immunized by VP6 protein of Example 1, 6-VLP and 2/6-VLP of Example 5 and rotavirus A obtained by MA104 cell culture, respectively, on development of diarrhea after infection of the neonatal mice with rotavirus.

FIG. 13 shows the effect and protection of the antibodies from the mother mice immunized by VP6 protein of Example 1, 6-VLP and 2/6-VLP of Example 5 and rotavirus A obtained by MA104 cell culture, respectively, on virus shedding after infection of neonatal mice with rotavirus, wherein A shows the virus titer in the intestine contents from different immunization groups, as measured by ELISA, B shows the percentage of virus reduction by shedding in different immunization groups as compared with the control group.

SEQUENCE INFORMATION

The information of sequences as involved in the invention is provided in the following Table 1.

TABLE 1

Primer list

| Primer name | Primer sequence |
|---|---|
| VP6-DF | GCTTTWAAACGAAGTCTTC |
| VP6-DR | GGTCACATCCTCTCACTA |
| VP6-1F | GGATCCCAT ATGGATGTCCTTTATTCTT |
| VP6-397R | AAGCTT TCATTTAATAAGCATGCT |

The invention is further illustrated by combining the following Examples. These Examples should not be construed as limiting the invention.

SPECIFIC MODES FOR CARRYING OUT THE INVENTION

The present invention is further illustrated in detail by reference to the examples as follows. It is understood by those skilled in the art that the examples are used only for the purpose of illustrating the present invention, rather than limiting the protection scope of the present invention. When the conditions are not indicated in the Examples, the Examples are carried out under the conventional conditions or the conditions recommended by the manufacturers. The reagents and instruments used in the present invention, the manufacturers of which are not indicated, are the conventional products that are commercially available.

Example 1: Expression and Purification of VP6 in *E. coli*

Preparation of VP6 Gene as a Template

Rotavirus strain (BEIJING WANTAI BIO-PHARMACEUTICAL CO., LTD.) was extracted with Trizol agent to get its genomic RNA. VP6-DR was used as a primer, and MMLV reverse transcriptase was used for reverse transcription. The reverse transcription was carried out at 55° C. in the following system for 30 min to get VP6 cDNA.

| RNA template | dNTP | VP6-DR | ddH2O | 5 × buffer | MML | RNAsin |
|---|---|---|---|---|---|---|
| 5 ul | 1 ul | 0.6 ul | 8.2 ul | 4 ul | 1 ul | 0.2 ul |

The cDNA obtained in the previous step was used as a template, VP6-DF was used as a forward primer, and VP6-DR was used as a reverse primer. The PCR reaction was performed to amplify VP6 gene in a PCR thermocycler (Biometra T3) under the following conditions.

| | |
|---|---|
| 94° C. denaturation for 5 min | 1 cycle |
| 94° C. denaturation for 30 s | |
| 56° C. annealing for 30 s | 35 cycles |
| 72° C. elongation for 90 s | |
| 72° C. elongation for 10 min | 1 cycle |

The PCR products of about 1.3 kb in length were obtained after amplification. Upon extraction with a gel extraction kit, the PCR products were ligated into the commercially available pMD 18-T vector (Takara), and were transformed into *E. coli* DH5α. The plasmids were extracted. After digestion with PstI/EcoR I, it was identified that positive clones containing VP6 genes, designated as PMD18-T-VP6F, were obtained.

M13F and M13R primers (Shanghai Boya Bio Co.) were used for sequencing. The results showed that the gene had an identity of above 90% to the corresponding gene of Rotavirus A.

Construction of a Non-Fusion Expression Vector Expressing VP6 Protein

The PMD18-T-VP6F obtained in the previous step was used as the template, VP6-1F was used as a forward primer, at the 5' terminal of which BamH I/Nde I enzyme cleavage site was introduced, and VP6-397R was used as a reverse primer, at the 5' terminal of which Hind III enzyme cleavage site was introduced. The PCR reaction was performed in a PCR thermocycler (Biometra T3) under the following conditions.

| | |
|---|---|
| 94° C. denaturation for 5 min | 1 cycle |
| 94° C. denaturation for 30 s | |
| 56° C. annealing for 30 s | 15 cycles |
| 72° C. elongation for 90 s | |
| 72° C. elongation for 10 min | 1 cycle |

The DNA fragments of about 1.2 kb in length were obtained after amplification. The fragments were ligated into the commercially available pMD 18-T vector, and were transformed into *E. coli* DH5α. The plasmids were extracted. After digestion with NdeI/Hind III enzyme, it was identified that positive clones containing VP6 genes, designated as PMD18-T-VP6, were obtained.

M13F and M13R primers (Shanghai Boya Bio Co.) were used for sequencing. The results show that the nucleotide sequence of the fragment of interest, which was inserted into PMD18-T-VP6, is 100% homologous to the sequence inserted into PMD18-T-VP6F.

The VP6 gene fragment was obtained by Nde I/Hind III enzymatic digestion of said PMD18-T-VP6 plasmid. The fragment was ligated into the prokaryotic expression vector Pet30a (Novagen) digested with Nde I/Hind III enzyme, and was transformed into *E. coli* DH5α. The plasmids were extracted. After digestion with NdeI/Hind III enzyme, it was identified that the plasmid P-VP6 having VP6 gene inserted was obtained.

Expression of VP6 Protein in *E. coli*

1 μL of the plasmid P-VP6 was used to transform *E. coli* BL21 (DE3). Single colonies were transferred to 4 ml liquid LB media containing kanamycin and were cultured at 37° C. with shaking until OD600 reached about 0.6. 0.5 ml bacterial solution was added to glycerol (a final concentration of 10%) and stored at −20° C. or −80° C. The remaining bacteria were added with IPTG to a concentration of 0.8 mM, and were further cultured at 37° C. for 2-4 h. Then, 1.5 mL bacteria were collected and were added with 100 uL ddH$_2$O to re-suspend the bacteria. 20 uL 6×Loading Buffer was added, mixed thoroughly, and was placed in a water-bath at 100° C. for 10 min. As identified by 10% SDS-PAGE, a protein band of about 45 KDa in size was clearly observed.

The bacteria carrying the recombinant plasmid P-VP6 obtained in the previous step were taken out from −80° C. refrigerator, were thawed, and then 5 μL were seeded in 50 mL LB medium containing kanamycin and incubated at 200 rpm and 37° C. overnight. The resultant solution was used as a seed solution. The seed solution was transferred to 15 flasks at a ratio of 1:1000, each of the flasks contained 500 mL Auto-Induction Medium (containing 10 g peptone, 5 g yeast powder, 10 g NaCl, 0.5 g glucose, 5 mL glycerol and 5 g α-lactose per liter, the pH of which was adjusted to neutral with NaOH solution), and was incubated in a shaking incubator at 180 rpm and 37° C. until the OD600 reached about 0.6. The temperature was then adjusted to 20° C., the bacteria were collected by centrifugation 20 h later, to get about 30 g bacteria expressing VP6 protein.

Preparation of VP6 Protein with a Purity of about 85%

Figure 1B:
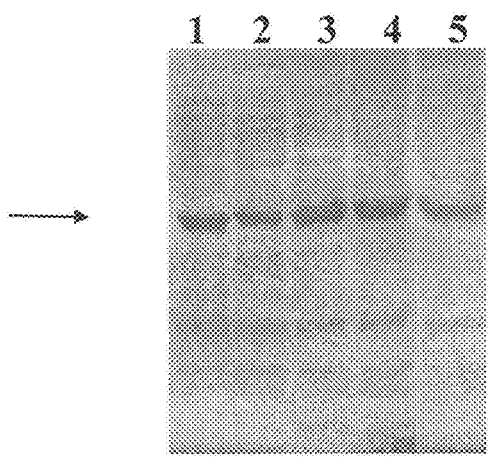
Figure 1C:
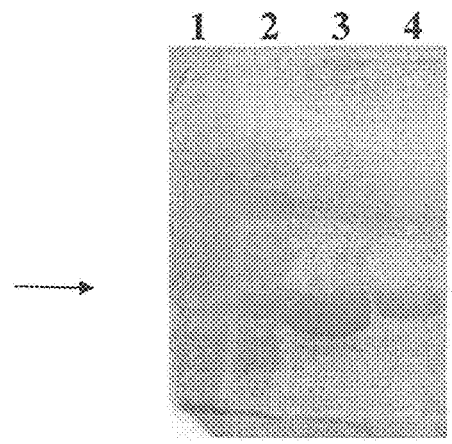

Bacteria were re-suspended at a proportion of 1 g bacteria corresponding to 15 ml lysis solution. Bacteria were disrupted by ultrasonication in an ice-water bath, for 4 min per 1 g bacteria, with a 4 s-interval every 2 s. The resultant solution was centrifuged at 13,000 rpm using JA-14 rotor for 15 min, and the supernatant was retained. The supernatant was subjected to 10% SDS-PAGE. At this stage, the VP6 protein in the supernatant had a purity of about 10% (as shown in FIG. 1, Lane 1).

The lysis supernatant was subpackaged into 1 ml per tube. To each tube, 0.05%-0.5% polyethyleneimine (PEI) or 10-100 mM $MnCl_2$, $MgCl_2$ or $CaCl_2$ was added, and the mixture was homogeneously mixed. Centrifugation was performed 30 min later, the supernatant was taken, and saturated ammonia sulfate was added to a concentration of 40%. After homogeneous mixing, standing for 0.5-2 h, and centrifugation, the supernatant was discarded. The precipitate was re-dissolved in 1/5 volume of buffer, and it was found by 10% SDS-PAGE that PEI or metal ion precipitation could remove a lot of nucleic acids and undesired proteins; after further purification and concentration posterior to ammonia sulfate precipitation, the purity of VP6 protein was greatly improved, wherein the purity was best improved at 20 mM $CaCl_2$ (as shown in FIG. 1B, Lane 2).

In an ice-water bath, to the solution of disrupted bacteria, 2M $CaCl_2$ solution was added under stirring to a final concentration of 20 mM. 30 min later, the resultant solution was centrifuged at 13,000 rpm using JA-14 rotor for 15 min, and the supernatant was retained. In an ice-water bath, solid ammonia sulfate was added under stirring to a saturation of 25%. The resultant mixture was placed in an ice-water bath for 1-2 h, and then was centrifuged at 13,000 rpm using JA-14 rotor for 15 min. The precipitate was kept and was re-suspended in 1/10 volume of 50 mM Tris-HCl buffer pH7.0+3M NaCl. The resultant mixture was centrifuged at 13,000 rpm using JA-14 rotor for 15 min, and the supernatant was kept. It was found by 10% SDS-PAGE that $CaCl_2$ precipitation could remove a lot of nucleic acids and undesired proteins, after further purification and concentration posterior to ammonia sulfate precipitation, the purity of VP6 protein was increased from 10% to about 85% (as shown in FIG. 1, Lanes 2 and 3).

Chromatographic Purification of VP6 Protein
Hydrophobic Interaction Chromatography
Equipment: AKTA Purifier UPC-100 preparative liquid chromatography system produced by GE Healthcare (i.e. the original Amershan Pharmacia Co.)
Chromatographic media: Phenyl Sepharose 6B High Performance (GE Healthcare Co.)
Column Volume: 5.5 cm×20 cm
Buffer: 50 mM Tris-HCl, pH7.0,
50 mM Tris-HCl, pH7.0+4M NaCl
Flow Rate: 8 mL/min
Detector Wavelength: 280 nm
Sample: VP6 protein solution in Example 1, which had a purity of about 85% and was filtered through a filter membrane with an aperture of 0.22 μm.
Elution protocol: eluting the protein of interest with 2M NaCl, eluting the undesired proteins with 50 mM Tris-HCl, pH7.0, collecting the eluate eluted with 2M NaCl, with a purity of about 98% as identified by 10% SDS-PAGE and Coomassie brilliant blue staining (as shown in FIG. 1, Lane 4); and the protein concentration and the nucleic acid content were determined by DU800, and the results were as follows: OD280 was 1.124, OD260 was 0.638, and OD320 was 0.006; after calculation in accordance with the formula, the protein concentration was 1.6 mg/mL, the nucleic acid content was below 0.25%, and the yield was above 50%.

Example 2: Expression and Purification of VP2 Protein in *E. coli*

P-VP2 plasmid was constructed by the applicant (Xiamen University, Li Tingdong, Prokaryotic expression of rotavirus structure protein and in vitro assembly of virus-like particles, 2009), and the expression strain was B121 (DE3). B121(DE3) was transformed with the P-VP2 plasmid, single colonies were picked and transferred to LB medium comprising kanamycin, and were cultured at 37° C. until OD600 reached about 0.6. 0.5 mL bacterial solution was added with glycerol to a final concentration of 10%, and was stored at −80° C. The bacteria carrying the plasmid P-VP2 in glycerol were taken out from −80° C. refrigerator, were thawed, and then were seeded in 50 mL LB medium comprising kanamycin and incubated under shaking at 37° C. overnight. The resultant solution was seeded and cultured in 500 mL LB medium comprising kanamycin until OD600 reached about 0.6. The temperature of the shaking table was adjusted to 25° C. Then the cultures were induced by adding 0.8 mM IPTG, and were further cultured for 6 h. The bacteria were collected.

The bacteria were re-suspended at a proportion of 1 g bacteria corresponding to 15 ml TB8.0+150 mM NaCl+0.5 mM EDTA. Bacteria were lysed by ultrasonication, and were centrifuged. The supernatant was collected. PEI was added to a final concentration of 0.25% under stirring. 30 min later, centrifugation was performed and the supernatant was collected. In an ice-water bath, saturated ammonia sulfate was added to a final concentration of 30%; stirring was performed for 1-2 h. After centrifugation, the precipitate was taken and was re-suspended in 1/10 volume of 50 mM Tris-HCl, pH8.0, and then was centrifuged. After centrifugation, the supernatant was taken. At this stage the VP2 had a purity of above 80% (as shown in FIG. 2, Lane 3).

Cation Exchange Chromatography
Equipment: AKTA Purifier UPC-100 preparative liquid chromatography system produced by GE Healthcare (i.e. the original Amershan Pharmacia Co.)
Chromatographic Media: SP Sepharose Fast Flow (GE Healthcare Co.)
Column Volume: 5.5 cm×20 cm
Buffer: 50 mM Tris-HCl, pH8.0,
50 mM Tris-HCl, pH8.0+2M NaCl
Flow Rate: 10 mL/min Detector Wavelength: 280 nm
Sample: VP2 protein solution in the last step, which had a purity of about 80%, and was filtered through a filter membrane with an aperture of 0.22 μm.
Elution protocol: eluting the undesired proteins with 150 mM NaCl, eluting the VP2 protein with 500 mM NaCl, collecting the eluate eluted with 500 mM NaCl, with a purity of about 95% as identified by 10% SDS-PAGE and Coomassie brilliant blue staining (as shown in FIG. 2, Lane 4), with a yield of above 50%.

Example 3: Identification of Rotavirus VP6 and VP2 Protein

The samples were the VP6 protein with a purity of above 98% obtained in Example 1 and VP2 protein with a purity of above 95% obtained in Example 2.
SDS-PAGE
The samples were treated in the following four manners, respectively: 1) the loading buffer comprising mercaptoethanol was used, and the samples were treated in a water bath at 100° C. for 10 min; 2) the loading buffer comprising mercaptoethanol was used; 3) the loading buffer free of mercaptoethanol was used, and the samples were treated in a water bath at 100° C. for 10 min; 4) the loading buffer free of mercaptoethanol was used. After separation by 10% SDS-PAGE, the protein was identified by coomassie brilliant blue staining. The SDS-PAGE results showed that the purified VP2 protein was present in a form of monomer or in a form of hydrophobic polymer, but the conformation was affected by disulfide bond, and VP6 was present in a form of polymer.
Size Exclusion Chromatographic Analysis
Equipment: AKTA Purifier UPC-100 preparative liquid chromatography system produced by GE Healthcare
Chromatographic column: Superdex200, 10 mm×300 mm (GE Healthcare), with a column volume of 24 mL
Buffer: Tris-HCl, pH8.0+500 mM NaCl for VP2; Tris-HCl, pH7.0+2M NaCl for VP6
Flow Rate: 0.5 mL/min
Detector Wavelength: $UV_{280\ nm}$
The results showed that the purified VP2 protein and VP6 protein each were a single component, and had a retention time of 27.34 and 33.91 min, respectively, and were homogenous.
Analytic Ultracentrifugation
The equipment was Beckman XL-A analytical ultracentrifuger, and the methods were sedimentation velocity method and sedimentation equilibrium method. Firstly, the sedimentation coefficients of VP2 protein and VP6 protein were analyzed by sedimentation velocity method, SEDIFIT software was used to carry out C(S) analysis, and the molecular weights of VP2 protein and VP6 protein were calculated primarily. The results showed that VP2 protein and VP6 protein might be present in a form of dimer and trimer, respectively. On the basis of this, the precise molecular weights of VP2 protein and VP6 protein were further analyzed by sedimentation equilibrium method. Origin Nonlin software and SEDPHAT software were used to analyze SE. The results showed that VP2 protein and VP6 protein had a molecular weight of 204±5.6 KDa and 114.9±1.6 KDa, respectively (FIG. 3C and FIG. 3D).
VP2 protein of native state is present in a form of dimer, and VP6 protein is present in a form of trimer, and their theoretic molecular weights are 205 KDa and 135 KDa, respectively. It was identified by analytic ultracentrifugation that the purified VP2 protein had a molecular weight of 204±5.6 KDa, which was consistent with the theoretic molecular weight. However, since SDS can interrupt hydrogen bond and hydrophobic interaction, VP2 in SDS-PAGE is mainly in a form of monomer. It was identified by analytic ultracentrifugation that the purified VP6 protein had a molecular weight of 114.9±1.6 KDa, and was present in a form of polymer in SDS-PAGE, which was between 119 and 211 KDa in size. According to the SDS-PAGE results in combination with the analytic ultracentrifugation results, the purified VP6 protein was present in a form of trimer. It was consistent with the result of size exclusion chromatography, i.e. the retention time of VP2 protein was shorter than that of VP6 protein. Accordingly, VP2 and VP6 protein obtained by prokaryotic expression retained their native confirmations. Moreover, the whole process was simple and was convenient for operation, and thus had incomparable advantages relative to eukaryotic expression.

Example 4: Assembly of VP2 Virus-Like Particle 2-VLP

The sample was the VP2 protein with a purity of above 95% obtained in Example 2.
Method: VP2 protein was dialyzed at 4° C. to an assembly buffer 50 mM TB8.0+0.2M $(NH_4)_2SO_4$, the buffer was changed every 12 h, and the dialysis was carried out for more than 24 h. After dialysis, the solution was centrifuged at 10000 rpm for 15 min, the precipitate was collected, and was dissolved in 50 mM TB8.0. The resultant solution was centrifuged at 10000 rpm for 15 min, and the supernatant was collected, i.e. monolayer virus-like particle 2-VLP consisting of VP2.

Example 5: Assembly of 6-VLP and 2/6-VLP

The samples were the VP6 protein with a purity of above 98% as obtained in Example 1, the VP2 protein with a purity of above 95% as obtained in Example 2, and 2-VLP as obtained in Example 4.
Assembly of 6-VLP
VP6 protein was dialyzed to the assembly buffer as shown in Table 2, and the buffer was changed every 12 h, and the dialysis was carried out for more than 24 h. Then centrifugation was carried out, and the supernatant was collected, i.e. 6-VLP.

TABLE 2

Assembly of 6-VLP in different buffer systems

|   | pH | NaCl concentration | Results |
|---|---|---|---|
| 1 | 3.0 | 0 | trimer |
| 2 | 3.0 | 0.5M | aggregation |
| 3 | 3.0 | 1M | aggregation |
| 4 | 4.0 | 0 | spherical particle |
| 5 | 4.0 | 0.2M | spherical particle |
| 6 | 4.35 | 0 | spherical particle |
| 7 | 4.35 | 0.5M | spherical particle |
| 8 | 4.35 | 1M | precipitant |
| 9 | 5.0 | 0 | spherical particle |
| 10 | 6.0 | 0 | spherical particle |
| 11 | 6.0 | 0.5M | spherical particle |

TABLE 2-continued

Assembly of 6-VLP in different buffer systems

|    | pH  | NaCl concentration | Results           |
|----|-----|--------------------|-------------------|
| 12 | 6.0 | 1M                 | spherical particle |
| 13 | 6.4 | 0.3M               | spherical particle |
| 14 | 7.0 | 0                  | trimer            |
| 15 | 7.0 | 0.5M               | trimer            |
| 16 | 7.0 | 1M                 | trimer            |

Assembly of 2/6-VLP

Process 1: 2-VLP and VP6 protein were mixed in a ratio of 1:3 by mass, and were dialyzed to CN4.0, CN5.0 or MES6.0, the buffer was changed every 12 h, and the dialysis was carried out for more than 24 h. After dialysis, the solution was centrifuged for 15 min at 10000 rpm, the supernatant was collected, i.e. 2/6-VLP.

Process 2: VP2 protein which was not assembled into VLP and VP6 protein were mixed in a given ratio, and were dialyzed to an assembly buffer (Table 3). The ratio of VP2 and VP6 was shown in table 4. The buffer was changed every 12 h, and the dialysis was carried out for more than 24 h. After dialysis, the solution was centrifuged at 10000 rpm for 15 min, and the supernatant was collected, i.e. 2/6-VLP.

TABLE 3

Assembly of 2/6-VLP in different buffer systems

|    | pH   | NaCl concentration | Results           |
|----|------|--------------------|-------------------|
| 1  | 3.0  | 0                  | polymer           |
| 2  | 4.35 | 0                  | 2/6-VLP           |
| 3  | 4.35 | 0.5M               | 2/6-VLP           |
| 4  | 6.0  | 0                  | 6-VLP             |
| 5  | 6.0  | 0.15M              | 6-VLP and 2/6-VLP |
| 6  | 6.0  | 0.3M               | 2/6-VLP           |
| 7  | 6.0  | 0.5M               | 2/6-VLP           |
| 8  | 6.4  | 0.3M               | 2/6-VLP           |
| 9  | 6.4  | 0.5M               | 2/6-VLP           |
| 10 | 6.4  | 1M                 | 2/6-VLP           |
| 11 | 7.0  | 0.3M               | polymer           |
| 12 | 8.0  | 0                  | polymer           |
| 13 | 8.0  | 0.5M               | polymer           |

TABLE 4

Ratio of VP2 and VP6 for assembly of 2/6-VLP

|    | VP2:VP6 | Results           |
|----|---------|-------------------|
| 1  | 1:2     | 2/6-VLP           |
| 2  | 1:2.2   | 2/6-VLP           |
| 3  | 1:2.4   | 2/6-VLP           |
| 4  | 1:2.6   | 2/6-VLP           |
| 5  | 1:2.8   | 2/6-VLP           |
| 6  | 1:3     | 2/6-VLP           |
| 7  | 1:4     | 6-VLP and 2/6-VLP |
| 8  | 1:5     | 6-VLP and 2/6-VLP |
| 9  | 1:6     | 6-VLP and 2/6-VLP |
| 10 | 1:8     | 6-VLP and 2/6-VLP |
| 11 | 1:10    | 6-VLP and 2/6-VLP |
| 12 | 0:1     | 6-VLP             |

Example 6: Morphologic Measurement of Rotavirus VLPs and Evaluation of Assembly Efficiency TEM Observation of Rotavirus VLPs The equipment was a JEOL 100 kV Transmission Electron Microscope (100,000× magnification). 2-VLPs obtained in Example 4 were fixed on a copper grid and negatively stained with 2% phosphotungstic acid at pH 7.4 for 30 min, and then was observed. A large number of hollow VLPs with a radius of 50-60 nm were observed (FIG. 4). 6-VLPs or 2/6-VLPs obtained in Example 5 were fixed on a copper grid and negatively stained with 2% phosphotungstic acid at pH 4.5 for 1 min, and then was observed. A large number of hollow VLPs with a radius of about 70 nm (FIG. 5A) and of about 60 nm (FIGS. 6B, 8A and 9A) were observed.

Dynamic Light-Scattering Observation of RV VLPs

DynaPro MS/X dynamic light-scattering instrument (including a temperature controller) produced by US Protein Solutions Co. was used for light-scattering measurements. The Regulation algorithm was used in the measurements. The samples were 6-VLP and 2/6-VLP obtained in Example 5. The samples were centrifuged at 12000 rpm for 10 min prior to the measurement. The results showed that 6-VLP and 2/6-VLP had a hydrodynamic radius of 40.36 nm (FIG. 5B) and of 34.27 nm (FIG. 9B), and had an assembly efficiency of 100%.

Analysis of RV VLPs by Size Exclusion Chromatography

Equipment: Agilent 1200 high performance liquid chromatograph (HPLC)

Chromatographic column: G5000PWXL 7.8 mm×30 cm (Japan TOSOH Co.), with a column volume of 13.4 ml Buffer: 20 mM phosphate buffer pH6.4+300 mM NaCl Flow rate: 0.5 ml/min Detection wavelength: 280 nm Sample: 6-VLP and 2/6-VLP obtained in Example 4

Figure 9C:
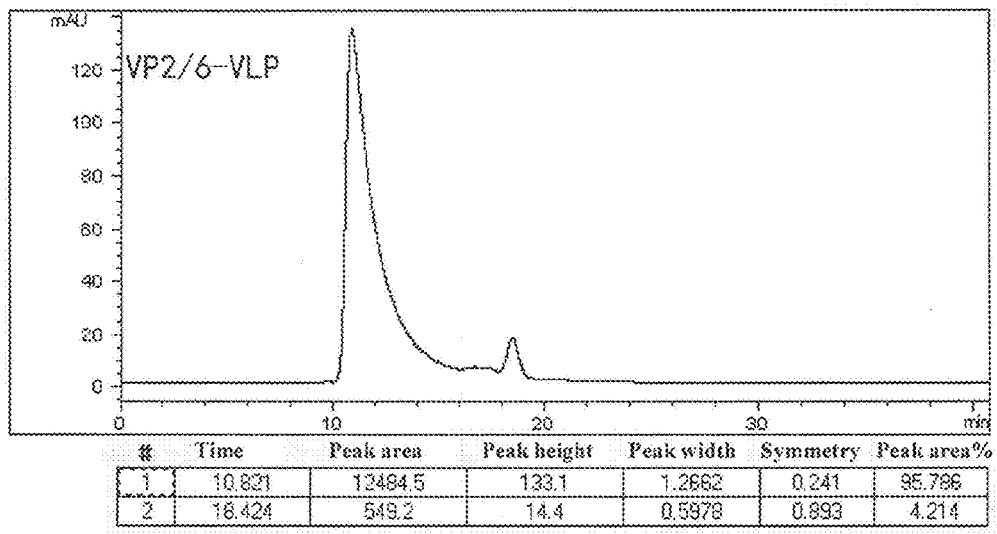

The results showed that 6-VLP had a retention time of 10.551 min and an assembly efficiency of 94.6% (FIG. 5C); 2/6-VLP had a retention time of 10.821 min and an assembly efficiency of 95.8% (FIG. 9C).

Analytical Ultracentrifugation of RV VLPs

Figure 6A:
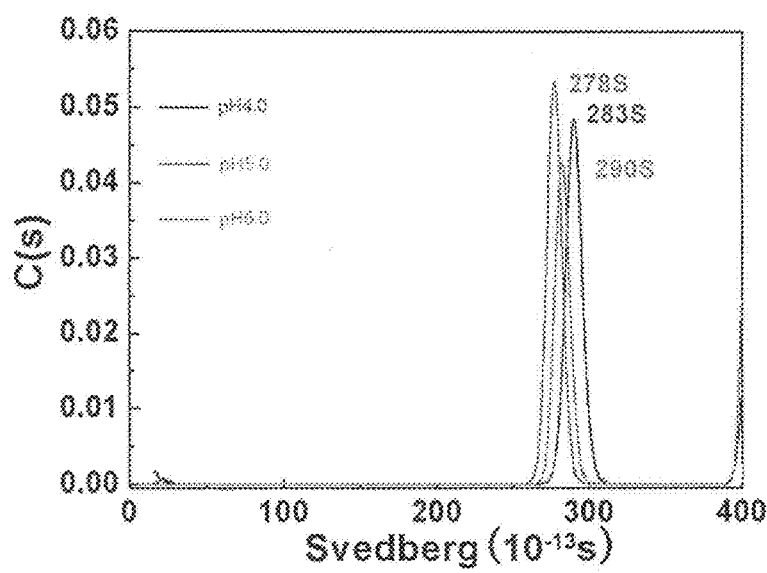
Figure 6B:
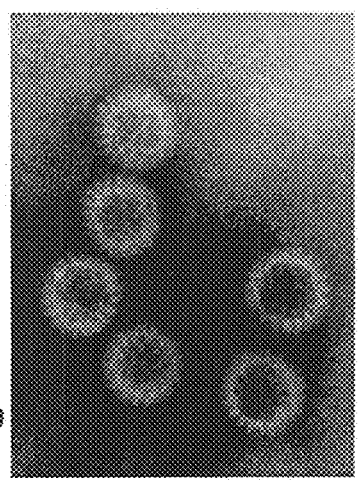

The equipment was Beckman XL-A analytical ultracentrifuger, the sample was 6-VLP and 2/6-VLP obtained in Example 5, the method was sedimentation velocity method, SEDIFIT software was used to analyze C(S). The results showed that at pH4.0-6.0, sedimentation velocities were different in different buffer systems to some extent, the sedimentation velocity of 6-VLP was between 237S and 240S, the sedimentation velocity of 2/6-VLP was between 278S and 290S, and both of them could be assembled at pH4.0-6.0 (FIG. 6A).

To sum up, 6-VLP and 2/6-VLP assembled in vitro had good homogeneity and an assembly efficiency of above 90%; their preparation processes were simple and convenient for operation; and they were obviously superior to virus-like particles of multiple different components produced by eukaryotic expression.

Example 7: Evaluation of Immunogenicity of VP6 Protein

The immunogenicity of VP6 protein was evaluated in a mouse model. The animals to be immunized were SPF grade female Balb/C mice of 5-8 weeks old (purchased from Shanghai Slac Laboratory Animal Co. Ltd), 3 mice per group, and the samples were VP6 protein obtained in Example 1, 6-VLP and 2/6-VLP obtained in Example 5 and rotavirus A obtained by MA104 cell culture. Said samples were mixed with an equal volume of Freund's adjuvant (complete Freund's adjuvant was used for primary immunization, and incomplete Freund's adjuvant was used for booster), the immunization dose was 100 μg, and the immunization route was subcutaneous immunization; or said samples were mixed with aluminum adjuvant, and the immunization dose was 1-100 μg, and the immunization route was muscular injection. The immunization procedure was as followed: the primary immunization at Day 0, and the boosters at Day 7 and Day 14.

Peripheral venous blood was taken from mice every week, serum was isolated, the titer of VP6 antibody in serum was determined by an EIA method. The procedure was as followed:
1) coating: the sample was VP6 protein obtained in Example 1, the buffer was 50 mM carbonate buffer pH9.6, the coating concentration was 500 ng/mL, the coating amount was 100 μL per well, and the coating condition was 37° C., 2 h;
2) washing: PBST (20 mM PBS+0.05% Tween20), once, drying by bottom up;
3) blocking: the blocking solution was PBS+0.5% casein, the blocking condition was 2004 per well, 37° C., 2 h; after blocking, drying by bottom up;
4) loading: sample: mouse serum; the diluent was PBS+10% calf serum; 10-fold serial dilution; 100 μL per well, 37° C., 30 min;
5) washing: PBST, 5 times, drying by bottom up:
6) adding an enzyme-labeled second antibody: the enzyme-labeled second antibody was GAM-HRP, the diluent was PBS+0.5% casein, the dilution fold was 1:5000, 100 μL per well, 37° C., 30 min;
7) washing: PBST, 5 times, drying by bottom up;
8) developing: TMB developing solution, 100 μL per well, 37° C., 15 min;
9) stopping: stop buffer, 50 μL per well;
10) readout: Antos enzyme-labeling equipment, OD450/600.

The greatest dilution fold, at which OD450/600 was of greater than 0.2, was determined as antibody titer in mouse serum. The results showed that as compared to an equal amount of inactivated virus, VP6 antigen had a higher immunogenicity; and Freund's adjuvant could better improve the immunogenicity of VP6 protein as compared to aluminum adjuvant (FIG. 10).

Example 8: Evaluation of Immune Protection of VP6 Protein and VLP Thereof

Since VP6 antibodies do not have in vitro neutralizing activity and adult mice have poor sensitivity to rotavirus, a pregnant mice-neonatal mice model is used to evaluate immune protection of VP6 protein. 4-5 week old SPF-grade female Balb/c mice were divided into five groups, VP6 obtained in Example 1, 6-VLP and 2/6-VLP obtained in Example 5, rotavirus A obtained by MA104 cell culture, or PBS was mixed with an equal volume of Freund's adjuvant (complete Freund's adjuvant was used for primary immunization, and incomplete Freund's adjuvant was used for booster), the immunization route was subcutaneous immunization, and the immunization dose was 10 μg VP6 per mouse. The immunization procedure was as followed: the primary immunization at Day 0, and the boosters at Day 10 and Day 20, and a final booster at Day 30 (using antigens in the same dose mixed with aluminum adjuvant by muscular injection). Peripheral venous blood was taken two weeks after the last immunization, and serum was isolated and stored for further detection. Female mice and male mice were kept in the same cage, and male mice were taken out after mating. Neonatal mice were challenged with a virus 4-6 days after birth, at a dose of $5*10^6$ TCID50 per neonatal mouse, wherein the virus was human rotavirus obtained by MA104 cell culture. After challenging with the virus, health condition of the neonatal mice was observed and recorded, such as diarrhea condition, and change in weight. A mouse was killed at each of 0, 24, 48 and 72 hpc, pathological changes in tissues of the mice were observed after anatomy, small intestine tissues were taken, and the virus was detected by methods such as immunohistochemistry and EIA. In addition, serum was isolated and titer of serum antibody was determined by EIA.

VP6 Immunogenicity and Passage of Maternal Antibody

Figure 11A:
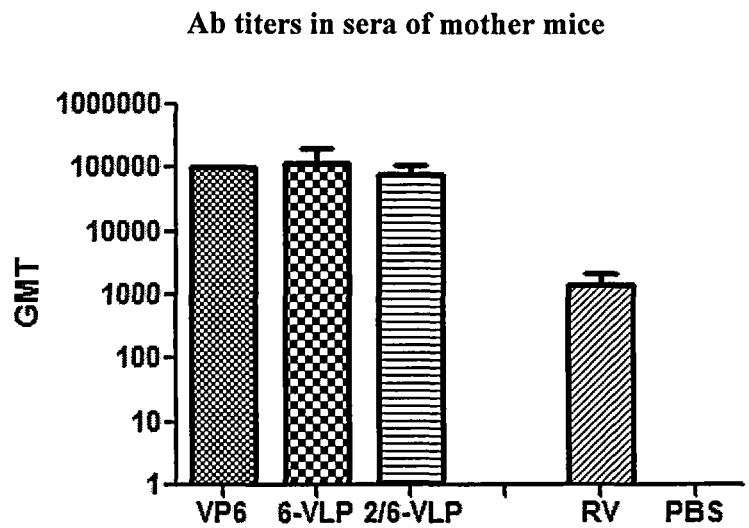
Figure 11B:
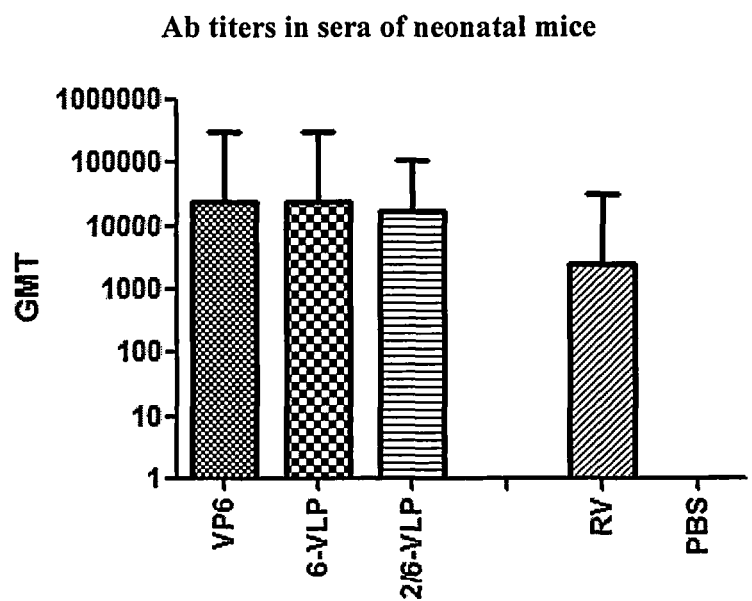

Titers of VP6 antibody were determined by EIA in sera of mother mice and neonatal mice from different immunization groups. The coated antigen was VP6 protein recombinantly expressed in *E. coli*, the coated amount was 50 ng/well, and the method was as described in Example 7. FIG. 11A showed the titers of VP6 antibody in sera of mother mice, wherein VP6, 6-VLP and 2/6-VLP all had a high immunogenicity and had no significant difference. FIG. 11B shows the titer of VP6 antibody in sera of neonatal mice, indicating that maternal antibody resulted from non-mucosa immunization was effectively passed to offspring via placenta and breast milk.

Protective Effect of VP6 Antibody from Mother Mice on Diarrhea of Neonatal Mice

After challenging with virus, diarrhea condition was monitored in neonatal mice. Mice were scored depending on the color and shape of feces, and it was found that diarrhea was most serious in neonatal mice 24 h after challenging with virus. The results were shown in Table 5. Within 24 h after challenging with virus, obvious diarrhea symptoms developed in the control group, while no diarrhea or only mild diarrhea symptoms developed in the experimental groups. Antibodies from mother mice immunized with VP6, 6-VLP, 2/6-VLP and inactivated virus alleviated the symptoms of diarrhea in neonatal mice, there was no significant difference among antibodies from mother mice immunized with VP6, 2/6-VLP and inactivated virus with respect to immune protection (P value was 0.070 and 0.946, respectively), while immune protection of 6-VLP was significantly lower than that of RV (P=0.001) and 2/6-VLP (P<0.001).

TABLE 5

| Diarrhea condition in neonatal mice 24 h after rotavirus infection | | | | | |
|---|---|---|---|---|---|
| Score | VP6 | 6-VLP | 2/6-VLP | RV | PBS |
| 1 | | | | | |
| 2 | 6 | | 12 | 7 | |
| 3 | 5 | 11 | 2 | 1 | 5 |
| 4 | 2 | 3 | | | 4 |
| 5 | 1 | | | | 4 |

1. Normal feces;
2. Brown shaped feces;
3. Brown-yellow soft feces;
4. Yellow, loose feces;
5. Watery feces Score≥3 was diagnosed as diarrhea, score>3 was diagnosed as serious diarrhea. FIG. 12 showed the ratio of diarrhea and serious diarrhea in progeny mice of different immunization groups; Table 6 showed protection efficiency of VP6 antibodies from mothers on diarrhea and serious diarrhea caused by rotavirus infectious in neonatal mice. The results showed that antibodies from mother mice immunized with VP6, 6-VLP, 2/6-VLP and inactivated virus could effectively prevent serious diarrhea caused by rotavirus infectious, and VP6, 6-VLP and 2/6-VLP had no significant difference as compared with inactivated virus with respect to immune protection (P value was 0.159, 0.159, 1.0, respectively); with respect to prevention of diarrhea, 2/6-VLP and the inactivated virus had the best protective effect, and had no significant difference (P=0.907), VP6 had a certain protective effect, which was significantly lower than that of the inactivated virus (P=0.04) and 2/6-VLP (P=0.018), while 6-VLP had no protective effect.

TABLE 6

Protection efficiency of VP6 antibodies from mother mice on diarrhea caused by rotavirus infectious

|  | Diarrhea | Serious diarrhea |
|---|---|---|
| VP6 | 42.86%* | 65.18%*, & |
|  | (−37.86%, 76.31%) | (−31.24%, 90.76%) |
| 6-VLP | / | 65.18%*, & |
|  |  | (−31.24%, 90.76%) |
| 2/6-VLP | 85.71%*, & | 100%*, & |
|  | (36.7%, 96.78%) | (?, 100%) |
| RV | 87.5%* | 100%* |
|  | (4.46%, 98.36%) | (?, 100%) |

*significant difference relative to PBS control;
&significant difference relative to inactivated RV Inhibition of VP6 Antibodies from Mother Mice on Replication of Rotavirus After challenging with virus, 1-2 neonatal mice were killed every 24 h, pathological change in tissues was observed, and it was found that intestinal tissues were aerated seriously in the control group. Intestinal tissues were taken and were grinded and disrupted by high pressure homogenization, and then centrifuged. The supernatant was taken, and VP6 antigen therein was determined by a sandwich method. The method was as followed:

1) coating: VP6 monoclonal antibody 9F10; the buffer was 20 mM PB7.4, the coating concentration was 4 μg/mL, the coating amount was 100 μL per well, and the coating condition was 37° C., 2 h;
2) washing: PBST (20 mM PBS+0.05% Tween20), 400 μL per well, once, drying by bottom up;
3) blocking: the blocking solution was 20 mM PBS+0.5% casein; the blocking condition was 200 μL per well, 37° C., 2 h; after blocking, drying by bottom up;
4) loading: diluting homogenate of small intestinal tissues with PBS+10% calf serum to 2-fold serial dilution, 100 μL per well, 37° C., 30 min;
5) washing: PBST, 5 times, 4004 per well, drying by bottom up;
6) adding an enzyme-labeled antibody: diluting HRP-labeled VP6 monoclonal antibody 15H10-HRP with diluent 20 mM PBS+0.5% casein by 5000 fold, 100 μL per well, 37° C., 30 min;
7) washing: PBST, 5 times, 400 μL per well, drying by bottom up;
8) developing: TMB developing solution, 100 μL per well, 37° C., 15 min;
9) stopping: stop buffer, 50 μL per well;
10) readout: Antos enzyme-labeling equipment, determining OD450/600, wherein the greatest dilution fold at which the OD450/600 value was greater than 0.2 was taken as a virus titer.

Figure 13A:
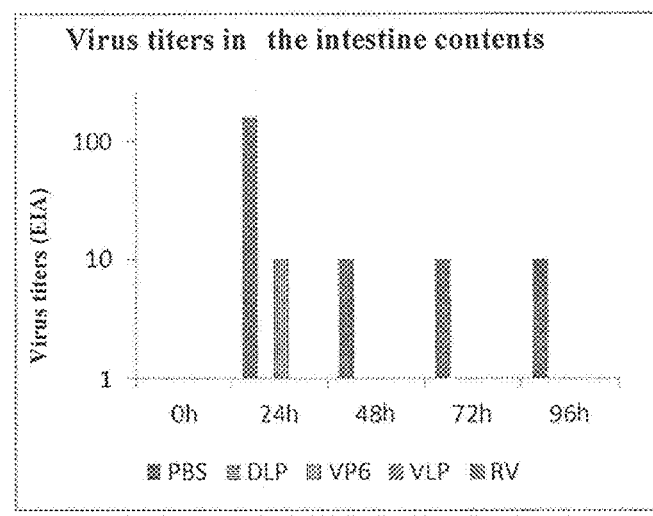
Figure 13B:
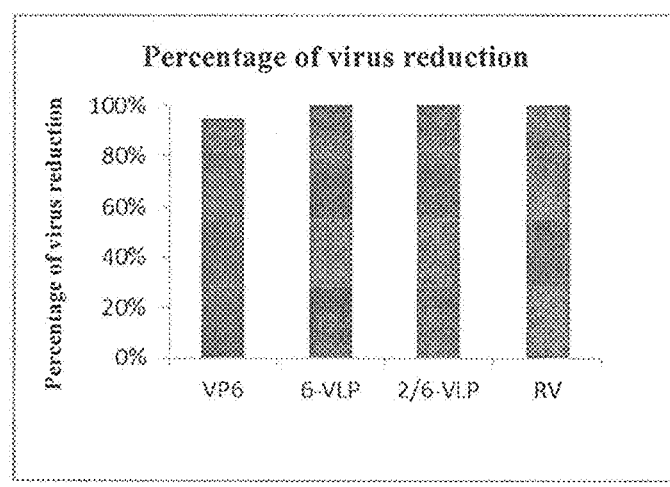

The results showed that VP6 antibodies could effectively inhibit the infection and replication of rotavirus. FIG. 13A showed the variation trend with time of viral titers in small intestine tissues after infection of neonatal mice from different immunization groups with rotavirus; and FIG. 13B showed the inhibition efficiency of VP6 antibodies on rotavirus replication, wherein maternal VP6 antibodies had an inhibition efficiency of 94.7% on rotavirus replication, while antibodies against 6-VLP, 2/6-VLP and the inactivated virus had an inhibition efficiency of 100%.

To sum up, the VP6, 6-VLP and 2/6-VLP antibodies from the mother mice had protective effect on rotavirus infection and diarrhea caused by rotavirus infection, wherein 2/6-VLP exhibited the best protective effect, and was not significantly different from inactivated virus in the same dose with respect to prevention of serious diarrhea and diarrhea.

Although the specific embodiments of the present invention have been described in details, those skilled in the art would understand that, according to the teachings disclosed in the specification, various modifications and changes can be made without departing from the spirit or scope of the present invention as generally described, and that such modifications and changes are within the scope of the present invention. The scope of the present invention is given by the appended claims and any equivalents thereof.

What is claimed is:

1. A method for preparing a double-layered virus-like particle of rotavirus comprising rotavirus VP2 protein and VP6 protein, the method comprising the following steps of:
   a) expressing VP6 in a soluble form in a prokaryotic expression system, and purifying the VP6, wherein the purified VP6 protein retains its native conformation and is present in a form of trimer; and
   b) co-assembling the purified VP6 with VP2 extracellularly, and with VP2 in a non-particulate state, to form a double-layered particle 2/6-VLP.

2. The method according to claim 1, wherein the VP6 protein is prepared by the following steps of:
   1) expressing a rotavirus VP6 protein in E. coli;
   2) to lysis supernatant comprising the VP6 protein, adding polyethylene imine (PEI) or an analog thereof, or a divalent or trivalent metal ion, to precipitate nucleic acids and some undesired proteins, wherein the concentration of PEI is between 0.05% and 0.2%, the metal ion includes $Mn^{2+}$, $Mg^{2+}$, $Ca^{2+}$, $Zn^{2+}$ and $Al^{3+}$, when used, the concentration of $Ca^{2+}$ is between 10 and 80 mM;
   3) performing centrifugation, and subjecting the lysis supernatant to salting-out and chromatographic purification.

3. The method according to claim 2, wherein the salting-out is performed using saturated ammonium sulfate.

4. The method according to claim 3, wherein the assembly of the double-layered virus-like particle 2/6-VLP comprises, mixing VP6 and VP2 proteins, then replacing the buffer with an assembly buffer to form a double-layered virus-like particle, wherein:
   a) VP2 and VP6 are purified proteins which are not assembled into particles and have a purity of above 95%;
   b) the assembly buffer is a phosphate buffer, a MES buffer or a citrate buffer, with a pH of between 3.0 and 7.0;
   c) the assembly buffer contains 0-2M NaCl; and
   d) the ratio of VP2 and VP6 by mass is between 1:1 and 1:10.

5. The method according to claim 4, wherein the assembly of the double-layered virus-like particle 2/6-VLP comprises, mixing VP6 and VP2 proteins, then replacing the buffer with an assembly buffer to form a double-layered virus-like particle, wherein:
   a) VP2 and VP6 are purified proteins which are not assembled into particles and have a purity of above 95%;
   b) the assembly buffer is a phosphate buffer, a MES buffer or a citrate buffer, with a pH of between pH 4.0 and pH 6.4;
   c) the assembly buffer contains 150 mM-2 M NaCl; and
   d) the ratio of VP2 and VP6 by mass is between 1:2 and 1:3.

6. The method according to claim 1, wherein the VP2 protein is VP2 protein in a non-particulate state prepared by the following steps:
   1) expressing rotavirus VP2 protein in E. coli;
   2) adding polyethyleneimine (PEI) to lysis supernatant containing the VP2 protein, wherein the concentration of PEI is between 0.05% and 1%;
   3) performing centrifugation, and purifying the lysis supernatant by salting-out and chromatography.

7. The method according to claim 6, wherein the salting-out is performed using ammonium sulfate.

8. The method according to claim 7, wherein the assembly of the double-layered virus-like particle 2/6-VLP comprises, mixing VP6 and VP2 proteins, then replacing the buffer with an assembly buffer to form a double-layered virus-like particle, wherein:
   a) VP2 and VP6 are purified proteins which are not assembled into particles and have a purity of above 95%;
   b) the assembly buffer is a phosphate buffer, a MES buffer or a citrate buffer, with a pH of between 3.0 and 7.0;
   c) the assembly buffer contains 0-2M NaCl; and
   d) the ratio of VP2 and VP6 by mass is between 1:1 and 1:10.

9. The method according to claim 8, wherein the assembly of the double-layered virus-like particle 2/6-VLP comprises, mixing VP6 and VP2 proteins, then replacing the buffer with an assembly buffer to form a double-layered virus-like particle, wherein:
   a) VP2 and VP6 are purified proteins which are not assembled into particles and have a purity of above 95%;

b) the assembly buffer is a phosphate buffer, a MES buffer or a citrate buffer, with a pH of between pH 4.0 and pH 6.4;
c) the assembly buffer contains 150 mM-2 M NaCl; and
d) the ratio of VP2 and VP6 by mass is between 1:2 and 1:3.

10. The method according to claim 1, wherein the assembly of the double-layered virus-like particle 2/6-VLP comprises, mixing VP6 and VP2 proteins, then replacing the buffer with an assembly buffer to form a double-layered virus-like particle, wherein:
a) VP2 and VP6 are purified proteins which are not assembled into particles and have a purity of above 95%;
b) the assembly buffer is a phosphate buffer, a MES buffer or a citrate buffer, with a pH of between 3.0 and 7.0;
c) the assembly buffer contains 0-2M NaCl; and
d) the ratio of VP2 and VP6 by mass is between 1:1 and 1:10.

11. The method according to claim 10, wherein the assembly of the double-layered virus-like particle 2/6-VLP comprises, mixing VP6 and VP2 proteins, then replacing the buffer with an assembly buffer to form a double-layered virus-like particle, wherein:
a) VP2 and VP6 are purified proteins which are not assembled into particles and have a purity of above 95%;
b) the assembly buffer is a phosphate buffer, a MES buffer or a citrate buffer, with a pH of between pH 4.0 and pH 6.4;
c) the assembly buffer contains 150 mM-2 M NaCl; and
d) the ratio of VP2 and VP6 by mass is between 1:2 and 1:3.

12. The method according to claim 2, wherein the chromatography includes hydrophobic interaction chromatography and ion exchange chromatography.

13. The method according to claim 12, wherein the assembly of the double-layered virus-like particle 2/6-VLP comprises, mixing VP6 and VP2 proteins, then replacing the buffer with an assembly buffer to form a double-layered virus-like particle, wherein:
a) VP2 and VP6 are purified proteins which are not assembled into particles and have a purity of above 95%;
b) the assembly buffer is a phosphate buffer, a MES buffer or a citrate buffer, with a pH of between 3.0 and 7.0;
c) the assembly buffer contains 0-2M NaCl; and
d) the ratio of VP2 and VP6 by mass is between 1:1 and 1:10.

14. The method according to claim 13, wherein the assembly of the double-layered virus-like particle 2/6-VLP comprises, mixing VP6 and VP2 proteins, then replacing the buffer with an assembly buffer to form a double-layered virus-like particle, wherein:
a) VP2 and VP6 are purified proteins which are not assembled into particles and have a purity of above 95%;
b) the assembly buffer is a phosphate buffer, a MES buffer or a citrate buffer, with a pH of between pH 4.0 and pH 6.4;
c) the assembly buffer contains 150 mM-2 M NaCl; and
d) the ratio of VP2 and VP6 by mass is between 1:2 and 1:3.

15. The method according to claim 12, wherein the chromatography is chromatography by Phenyl HP (GE) under the condition of 3M NaCl, wherein nucleic acids pass through the column, VP6 protein is eluted under the condition of 2M NaCl, and the undesired protein is eluted under the condition of no salts.

16. The method according to claim 2, wherein the assembly of the double-layered virus-like particle 2/6-VLP comprises, mixing VP6 and VP2 proteins, then replacing the buffer with an assembly buffer to form a double-layered virus-like particle, wherein:
a) VP2 and VP6 are purified proteins which are not assembled into particles and have a purity of above 95%;
b) the assembly buffer is a phosphate buffer, a MES buffer or a citrate buffer, with a pH of between 3.0 and 7.0;
c) the assembly buffer contains 0-2M NaCl; and
d) the ratio of VP2 and VP6 by mass is between 1:1 and 1:10.

17. The method according to claim 16, wherein the assembly of the double-layered virus-like particle 2/6-VLP comprises, mixing VP6 and VP2 proteins, then replacing the buffer with an assembly buffer to form a double-layered virus-like particle, wherein:
a) VP2 and VP6 are purified proteins which are not assembled into particles and have a purity of above 95%;
b) the assembly buffer is a phosphate buffer, a MES buffer or a citrate buffer, with a pH of between pH 4.0 and pH 6.4;
c) the assembly buffer contains 150 mM-2 M NaCl; and
d) the ratio of VP2 and VP6 by mass is between 1:2 and 1:3.

18. The method according to claim 2, wherein the concentration of PEI is 0.1% and the metal ion is $Ca^{2+}$ with a concentration of 20 mM.

19. The method according to claim 6, wherein the chromatography includes ion exchange chromatography and hydrophobic interaction chromatography.

20. The method according to claim 19, wherein the assembly of the double-layered virus-like particle 2/6-VLP comprises, mixing VP6 and VP2 proteins, then replacing the buffer with an assembly buffer to form a double-layered virus-like particle, wherein:
a) VP2 and VP6 are purified proteins which are not assembled into particles and have a purity of above 95%;
b) the assembly buffer is a phosphate buffer, a MES buffer or a citrate buffer, with a pH of between 3.0 and 7.0;
c) the assembly buffer contains 0-2M NaCl; and
d) the ratio of VP2 and VP6 by mass is between 1:1 and 1:10.

21. The method according to claim 20, wherein the assembly of the double-layered virus-like particle 2/6-VLP comprises, mixing VP6 and VP2 proteins, then replacing the buffer with an assembly buffer to form a double-layered virus-like particle, wherein:
a) VP2 and VP6 are purified proteins which are not assembled into particles and have a purity of above 95%;
b) the assembly buffer is a phosphate buffer, a MES buffer or a citrate buffer, with a pH of between pH4.0 and pH6.4;
c) the assembly buffer contains 150 mM-2 M NaCl; and
d) the ratio of VP2 and VP6 by mass is between 1:2 and 1:3.

22. The method according to claim 19, wherein the chromatography is chromatography by SP FF (GE) under the condition of Tris-HCl (pH 8.0), wherein nucleic acids and some undesired proteins pass through the column or are eluted under the condition of 150 mM NaCl, and VP2 protein is eluted under the condition of 500 mM NaCl.

23. The method according to claim 6, wherein the assembly of the double-layered virus-like particle 2/6-VLP comprises, mixing VP6 and VP2 proteins, then replacing the buffer with an assembly buffer to form a double-layered virus-like particle, wherein:
  a) VP2 and VP6 are purified proteins which are not assembled into particles and have a purity of above 95%;
  b) the assembly buffer is a phosphate buffer, a MES buffer or a citrate buffer, with a pH of between 3.0 and 7.0;
  c) the assembly buffer contains 0-2M NaCl; and
  d) the ratio of VP2 and VP6 by mass is between 1:1 and 1:10.

24. The method according to claim 23, wherein the assembly of the double-layered virus-like particle 2/6-VLP comprises, mixing VP6 and VP2 proteins, then replacing the buffer with an assembly buffer to form a double-layered virus-like particle, wherein:
  a) VP2 and VP6 are purified proteins which are not assembled into particles and have a purity of above 95%;
  b) the assembly buffer is a phosphate buffer, a MES buffer or a citrate buffer, with a pH of between pH 4.0 and pH 6.4;
  c) the assembly buffer contains 150 mM-2 M NaCl; and
  d) the ratio of VP2 and VP6 by mass is between 1:2 and 1:3.

* * * * *

SEQUENCE LISTING

```
<160> NUMBER OF SEQ ID NOS: 4

<210> SEQ ID NO 1
<211> LENGTH: 19
<212> TYPE: DNA
<213> ORGANISM: artificial
<220> FEATURE:
<223> OTHER INFORMATION: Synthetic oligonucleotide: primer

<400> SEQUENCE: 1
gctttwaaac gaagtcttc                                              19

<210> SEQ ID NO 2
<211> LENGTH: 18
<212> TYPE: DNA
<213> ORGANISM: artificial
<220> FEATURE:
<223> OTHER INFORMATION: Synthetic oligonucleotide: primer

<400> SEQUENCE: 2
ggtcacatcc tctcacta                                               18
```

```
<210> SEQ ID NO 3
<211> LENGTH: 28
<212> TYPE: DNA
<213> ORGANISM: artificial
<220> FEATURE:
<223> OTHER INFORMATION: Synthetic oligonucleotide: primer

<400> SEQUENCE: 3
ggatcccata tggatgtcct ttattctt                                    28

<210> SEQ ID NO 4
<211> LENGTH: 24
<212> TYPE: DNA
<213> ORGANISM: artificial
<220> FEATURE:
<223> OTHER INFORMATION: Synthetic oligonucleotide: primer

<400> SEQUENCE: 4
aagctttcat ttaataagca tgct                                        24
```